US011274328B2

(12) United States Patent
Wang et al.

(10) Patent No.: US 11,274,328 B2
(45) Date of Patent: Mar. 15, 2022

(54) METHODS FOR PRODUCING REBAUDIOSIDE D AND REBAUDIOSIDE M AND COMPOSITIONS THEREOF

(71) Applicant: SICHUAN INGIA BIOSYNTHETIC CO., LTD., Sichuan (CN)

(72) Inventors: Yong Wang, Chengdu (CN); Jun Hua, Chengdu (CN); Liang Pei, Chengdu (CN)

(73) Assignee: SICHUAN INGIA BIOSYNTHETIC CO., LTD., Sichuan (CN)

(*) Notice: Subject to any disclaimer, the term of this patent is extended or adjusted under 35 U.S.C. 154(b) by 136 days.

(21) Appl. No.: 16/588,427

(22) Filed: Sep. 30, 2019

(65) Prior Publication Data

US 2020/0102589 A1 Apr. 2, 2020

(30) Foreign Application Priority Data

Sep. 29, 2018 (CN) .......................... 201811148603.0
Sep. 29, 2018 (CN) .......................... 201811148626.1
Sep. 29, 2018 (CN) .......................... 201811148627.6
Sep. 29, 2018 (CN) .......................... 201811148647.3

(51) Int. Cl.
*C12P 19/56* (2006.01)
*A23L 27/30* (2016.01)
*C12N 1/20* (2006.01)
*C07H 15/256* (2006.01)

(52) U.S. Cl.
CPC .............. *C12P 19/56* (2013.01); *A23L 27/36* (2016.08); *C07H 15/256* (2013.01); *C12N 1/20* (2013.01)

(58) Field of Classification Search
CPC .......... C12P 19/56; C12P 19/18; A23L 27/36; C12N 1/20; C07H 15/256; C07H 1/00
See application file for complete search history.

(56) References Cited

U.S. PATENT DOCUMENTS

| 2008/0300402 A1* | 12/2008 | Yang | .................... A23L 33/105 536/128 |
| 2011/0092684 A1* | 4/2011 | Abelyan | ................ C07H 15/24 536/18.1 |
| 2016/0186225 A1* | 6/2016 | Mikkelsen | .............. A23L 27/36 426/590 |

FOREIGN PATENT DOCUMENTS

| CN | 102559528 A | 7/2012 |
| CN | 103031283 B | * 4/2013 |
| CN | 105051195 A | 11/2015 |
| CN | 105200098 A | 12/2015 |
| CN | 106834389 A | 6/2017 |
| CN | 107404919 A | 11/2017 |
| CN | 107949632 A | 4/2018 |
| WO | WO-2013-036366 A1 | * 3/2013 |
| WO | WO-2014-122227 A2 | * 8/2014 |
| WO | 2018/112189 A1 | 6/2018 |

OTHER PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10:8-9.*
Gong et al. Degradation kinetics of rebaudioside A in various buffer solutions. International Journal of Food Science & Technology (2013), 48: 2500-2505.*

* cited by examiner

*Primary Examiner* — Iqbal H Chowdhury
(74) *Attorney, Agent, or Firm* — Oliff PLC

(57) ABSTRACT

The invention relates to methods for producing rebaudioside D and/or rebaudioside M, and compositions comprising the same. The invention provides a method for producing RD and/or RM compositions. The method comprises using rebaudioside A and/or stevioside as substrate and a recombinant microorganism or an enzyme produced by the recombinant microorganism or a metabolite of the recombinant microorganism to catalyze the reaction of the substrate in the presence of sucrose and trisodium citrate and produce a mixture of rebaudioside D and rebaudioside M, and then separates and purifies the mixture to obtain rebaudioside D or rebaudioside M.

28 Claims, No Drawings

Specification includes a Sequence Listing.

METHODS FOR PRODUCING REBAUDIOSIDE D AND REBAUDIOSIDE M AND COMPOSITIONS THEREOF

CROSS REFERENCE TO RELATED APPLICATIONS

This application is claims benefit of CN 109393426, filed on Sep. 29, 2018; CN 109234340, filed on Sep. 29, 2018; CN 109234341, filed on Sep. 29, 2018; and CN 109349596, filed on Sep. 29, 2018; each of which is hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 30, 2019, is named 20190930_SL.txt and it is 50,354 bytes in size.

FIELD OF THE INVENTION

This invention relates to methods for producing rebaudioside D (reb D) and rebaudioside M (reb M), specifically belonging to the technical field of food additives.

BACKGROUND

Currently, the most commonly used natural sweetener is sucrose. It gives sweet taste and is generally accepted. However, sucrose is high in calories and should be strictly controlled in the diet of diabetics and obese individuals. High intensity sweeteners possess a sweetness level that is many times greater than the sweetness level of sucrose. High intensity sweeteners such as steviol glycosides do not elicit a glycemic response, making them suitable for use in products targeted to diabetics, obese groups and others interested in controlling for their intake of carbohydrates.

However, the high intensity sweeteners generally used as sugar (sucrose) substitutes possess taste characteristics different from those of sugar. The taste characteristics that differ from those of sugar may include the temporal profile of the sweet taste, maximal response, flavor profile, mouthfeel, and adaptation behavior. For example, the sweet taste of some high-potency sweeteners are slower in onset and longer in duration than the sweet taste produced by sugar and thus change the taste balance of a food composition. Because of these differences, the use of high-potency sweeteners to replace a bulk sweetener such as sugar, in a food or beverage, may cause an imbalance in the temporal and/or flavor profile. If the taste profile of high-potency sweeteners could be modified to impart desired taste characteristics, high-potency sweeteners could be used to provide more desirable taste characteristics to low calorie beverages and food products.

Although methods are known for preparing steviol glycosides from *Stevia rebaudiana*, many of these methods are unsuitable for commercial use. Accordingly, there remains a need for simple, efficient, and economical methods for preparing compositions comprising steviol glycosides, including highly purified steviol glycoside compositions with improved flavor profiles.

SUMMARY OF THE INVENTION

In one aspect, the present invention provides a method for producing rebaudioside D and/or rebaudioside M, comprising:

providing a starting composition comprising at least one of rebaudioside A and stevioside;

incubating the starting composition with a recombinant microorganism in a mixture, wherein the recombinant microorganism expresses an EUGT11 enzyme and a UGT76G1 enzyme; and purifying rebaudioside D and/or rebaudioside M from the mixture.

In one aspect, the present invention provides a method for producing rebaudioside D and/or rebaudioside M, comprising:

providing a starting composition comprising at least one of rebaudioside A and stevioside;

incubating the starting composition with an enzyme preparation produced by a recombinant microorganism in a mixture, wherein the recombinant microorganism expresses an EUGT11 enzyme and a UGT76G1 enzyme;

purifying rebaudioside D and/or rebaudioside M from the mixture.

In some embodiments, the incubating step is performed in the presence of sucrose and trisodium citrate.

In some embodiments, the recombinant microorganism is recombinant *Escherichia coli*, recombinant *Pichia pastoris*, recombinant *Bacillus subtilis*, recombinant *Corynebacterium glutamicum* or recombinant streptomycete.

In some embodiments, the recombinant microorganism is recombinant *Escherichia coli*.

In some embodiments, pgm gene, glgC gene and agp gene in the recombinant *Escherichia coli* are knocked out, and the UDPG synthetase gene ushA are replaced with T5 operon containing Basp and ugpA genes.

In some embodiments, the recombinant microorganism is recombinant *Pichia pastoris*.

In some embodiments, pgm gene, glgC gene and agp gene in the recombinant *Pichia pastoris* are knocked out.

In some embodiments, the recombinant microorganism is a whole cell and the mixture in which the starting composition and the recombinant microorganism are incubated is a cell culture medium.

In some embodiments, the enzyme preparation is a crude enzyme preparation produced by the recombinant microorganism.

In some embodiments, the crude enzyme preparation contains glucosyltransferase and some secondary metabolites.

In some embodiments, the crude enzyme preparation is produced by cell disruption in the presence of great than 40% of sucrose as a hypertonic solution.

In some embodiments, the starting composition and the recombinant microorganism or the enzyme preparation produced thereof are incubated under one or more of the following conditions:

pH of 7-8, the amount of recombinant microorganism or the enzyme preparation constitutes 5%-30% by wet weight (w/v) of the mixture, the at least one of rebaudioside A and stevioside is present at a concentration of 1-100 g/L;

trisodium citrate is present at 50-80 mM; and sucrose is present at 30-90% (w/v).

In some embodiments, the amount of recombinant microorganism or the enzyme preparation constitutes 15% of the mixture, the at least one of rebaudioside A and stevioside is present at a concentration of 30 g/L; trisodium citrate is present at 60 mM, sucrose is present at 50% (w/v), and the pH is 7.3.

In some embodiments, the incubating step is performed at a temperature between 35-40° C. for a duration of 10-240 hours.

In some embodiments, the temperature is 39.5° C. and the duration is 120 hours.

In some embodiments, purifying rebaudioside D and/or rebaudioside M from the mixture comprises the following steps:

(a) heating, macro-filtering and ultra-filtering the mixture to obtain an ultrafiltrate;

(b) separating rebaudioside D and/or rebaudioside M from the ultrafiltrate by nanofiltration to obtain a retentate; and (c) obtaining purified and concentrated rebaudioside D and/or rebaudioside M by concentrating the retentate to crystal and drying; or concentrating the retentate and spray-drying.

In some embodiments, the ultrafiltration membrane used in Step a has a specification of 10 kD with the transmembrane pressure of 1.0-1.5 MPa.

In some embodiments, the nanofiltration membrane used in Step b has a specification of 0.5 kD with the transmembrane pressure of 1.5-2.0 MPa.

In some embodiments, the crystallization method used in step c comprises: concentrating the retentate to a liquid with the solid content of 10-30%, adding ethanol to adjust the ethanol concentration to 10-80%, heating to boil, cooling to 0-40° C. and crystallizing for 1-60 h.

In some embodiments, the spray-drying in step c is performed under a condition in which the retentate is concentrated to a liquid with the solid content of 10-60% and then spray-dried with a temperature of 80° C. at the air inlet and 120° C. at the air outlet during spray-drying.

In some embodiments, the purification step does not involve a multi-column system.

In some embodiments, the method does not involve a step of purifying the recombinant microorganism from a cell culture.

In some embodiments, the method does not involve a step of purifying the EUGT11 enzyme or the UGT76G1 enzyme.

In one aspect, the present invention provides a sweetener composition comprising rebaudioside D and/or rebaudioside M produced by a method described herein.

In one aspect, the present invention provides a sweetener composition comprising rebaudioside D and rebaudioside M at a ratio of rebaudioside D:rebaudioside M of 1.5-9:1 by weight.

In some embodiments, the ratio of rebaudioside D:rebaudioside M is 3-9:1 by weight.

In some embodiments, the ratio of rebaudioside D:rebaudioside M is 3:1 by weight.

In some embodiments, the sweetener further comprising rebaudioside A.

In some embodiments, the ratio of rebaudioside D and rebaudioside M combined: rebaudioside A ranges from 1:9-9:1 by weight.

In some embodiments, the ratio of rebaudioside D and rebaudioside M combined: rebaudioside A is 3:7-7:3 by weight.

In some embodiments, the ratio of rebaudioside D and rebaudioside M combined: rebaudioside A is 4:6-6:4 by weight.

In one aspect, the present invention provides a method of producing a sweetener composition, comprising incubating rebaudioside A with a recombinant microorganism in the presence of sucrose, zinc chloride and trisodium citrate, wherein the recombinant microorganism is present at a cell concentration OD600 of 80-120, wherein the concentration of rebaudioside A, trisodium citrate, zinc chloride and sucrose is 1-80 g/L, 50-80 mmol/L, 0.5-2 mmol/L and 30-50% (W/V) respectively, the pH value is 7.5-8.5, and the recombinant microorganism expresses an EUGT11 enzyme and a UGT76G1 enzyme.

In some embodiments, the incubation temperature is 35-40° C. and the incubation time is 20-60 hours.

In some embodiments, the cell concentration OD600 of the recombinant microorganism is 100, the concentration of rebaudioside A, trisodium citrate, zinc chloride and sucrose is 5 g/L, 60 mmol/L, 1 mmol/L and 40% (W/V) respectively, and the pH value is 8.0.

In some embodiments, the incubation temperature is 37° C. and the incubation time is 24 hours.

In some embodiments, the recombinant microorganism is recombinant *Escherichia coli*, recombinant yeast, recombinant *Bacillus subtilis*, recombinant *Corynebacterium glutamicum* or recombinant *Streptomyces*.

In some embodiments, the ratio of rebaudioside D:rebaudioside M is 3-9:1 by weight.

In some embodiments, the ratio of rebaudioside D:rebaudioside M is 3:1. When RD and RM are mixed at a ratio of 3:1, the sweetener composition is similar to sucrose in taste.

In some embodiments, the ratio of rebaudioside D:rebaudioside M is 9:1. When RD and RM are mixed at a ratio of 9:1, the sweetener composition is very similar to sucrose in taste. Both RD and RM in the invention are highly pure, and the purity thereof is over 95% (w/w).

In some embodiments, the invention also provides another sweetener composition, i.e., sweetener composition II, which is prepared by mixing the sweetener composition I with rebaudioside A at a ratio of sweetener composition I: rebaudioside A of 1-9:1-9 by weight. The inventor found that the taste is better after RA, RD and RM are mixed at a certain ratio.

Preferably, the ratio of sweetener composition I: rebaudioside A is 3-7:3-7 by weight; at such ratio, the resulting composition is very similar to sucrose in taste.

More preferably, the ratio of sweetener composition I: rebaudioside A is 4-6:4-6 by weight; at such ratio, the resulting composition has no difference in taste from sucrose.

In addition, the sweetener composition of the invention can also be prepared by mixing the sweetener composition I with other sugar alcohol sweeteners, for example, the sweetener composition can be mixed with erythritol to inhibit bitterness and reduce sweetness factor, or mixed with xylitol.

The purity of RA in the invention is over 97% (w/w).

The sweetener composition of the invention can be prepared by simple mixing, for example, directly weighing rebaudioside D (>95%, w/w) and rebaudioside M (>95%, w/w) and mixing in a proportion.

Certain Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to methods well known in the art and as described in various general and more specific references that are cited and discussed throughout the present specification. See e.g., Sambrook et al. *Molecular Cloning*: A Laboratory Manual (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Homologous: When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89.

For example, in some instances the following six groups each contain amino acids that are conservative substitutions for one another: 1) Serine, Threonine; 2) Aspartic Acid, Glutamic Acid; 3) Asparagine, Glutamine; 4) Arginine, Lysine; 5) Isoleucine, Leucine, Methionine, Alanine, Valine, and 6) Phenylalanine, Tyrosine, Tryptophan. Other appropriate substitutions are known to the person of ordinary skill in the art in addition to the non-limiting examples described herein.

Biocatalysis or biocatalytic: as used herein, "biocatalysis" or "biocatalytic" refers to the use of natural catalysts, such as protein enzymes, to perform chemical transformations on organic compounds. Biocatalysis is alternatively known as biotransformation or biosynthesis. Both isolated and whole-cell biocatalysis methods are known in the art. Biocatalyst protein enzymes can be naturally occurring or recombinant proteins. As used herein, the term biotransformation may be described as transformation or molar transformation.

Carbohydrate: The term "carbohydrate" generally refers to aldehyde or ketone compounds substituted with multiple hydroxyl groups, of the general formula $(CH_2O)n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Highly purified target steviol glycoside(s), particularly, reb D and/or reb M obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components. In some embodiments, the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, it may be desirable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Comparable: The term "comparable" as used herein, refers to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Highly purified: as used herein, the term "highly purified" refers to a composition having greater than about 80% by weight of the target steviol glycoside on an anhydrous basis. In some embodiment, the highly purified target steviol glycoside composition comprises greater than about 90% by weight of the target steviol glycoside on an anhydrous basis, such as, for example, 91% greater than about 92%, greater than about 93%, greater than about 94%, greater than about 95%, greater than about 95%, greater than about 97%, greater than about 98% or greater than about 99% target steviol glycoside content on a dry basis.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical or at least 80%, 85%, 90%, 95%, or 99% identical. In some embodiments, a nucleic acid sequence or amino acid sequence is substantially identical to a reference sequence in that it is either identical in sequence or contains between 1-5 substitutions as compared with the reference sequence. For example, in some embodiments, an amino acid sequence is substantially identical to a reference amino acid sequence in that it is either identical in sequence or contains between 1-5 amino acid substitutions as compared with the reference sequence. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, or reduce: As used herein, the terms "improve," "increase" or "reduce," or grammatical equivalents, indicate values that are relative to a baseline measurement, such as a measurement of a flavor profile prior to compositions or methods described herein, or a measurement in a control individual (or multiple control individuals) in the absence of compositions or methods described herein. A "control individual" is an individual used to evaluate the flavor profile of a sweetener described herein.

Isolated: as used herein, refers to a substance and/or entity (e.g. a nucleic acid or a polypeptide) that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Nucleic acid: as used herein, the term "nucleic acid" refers to a polymer of at least three nucleotides. In some embodiments, a nucleic acid comprises DNA. In some embodiments comprises RNA. In some embodiments, a nucleic acid is single stranded. In some embodiments, a nucleic acid is double stranded. In some embodiments, a nucleic acid can contain non-natural or altered nucleotides. The terms "nucleic acid" and "polynucleotide" as used herein can refer to a polymeric form of nucleotides of any length, either ribonucleotides (RNA) or deoxyribonucleotides (DNA). These terms can refer to the primary structure of the molecule, and thus include double- and single-stranded DNA, and double- and single-stranded RNA. The terms can include, as equivalents, analogs of either RNA or DNA made from nucleotide analogs and modified polynucleotides such as, though not limited to, methylated and/or capped polynucleotides. Nucleic acids can be linked via phosphate bonds to form nucleic acid sequences or polynucleotides, though many other linkages are known in the art (e.g., phosphorothioates, boranophosphates, and the like).

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Starting composition: As used herein, "starting composition" refers to any composition (generally an aqueous solution) containing one or more steviol glycosides, where the one or more steviol glycosides serve as the substrate for the biotransformation or biocatalysis.

Steviol glycoside(s): As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside N, rebaudioside O, synthetic steviol glycosides, e.g. enzymatically glucosylated steviol glycosides and combinations thereof. As used herein, the term "rebaudioside" and "reb" are used interchangeably to refer to a rebaudioside compound.

DETAILED DESCRIPTION

According to the present invention, engineered yeast are employed to prepare RD and RM. The method comprises using glucose, nitrogen source, potassium source, magnesium source, phosphorus source, trace metal, vitamin and defoamer to prepare fermentation medium at the pH of 5.8 or above, preferably at 5.8-6.2, and employing the engineered yeast to ferment the medium to obtain one or more steviol glycosides. By using this method, a mixture of more steviosides, including rubusoside, stevioside, RA, RD, RE, RM and RI, will be produced.

Despite the low calorie and high sweetness, stevioside and rebaudioside A still have a bitter taste after the sweetness, and thus the taste and flavor are not comparable to those of sucrose. Although rebaudioside D has a similar taste to sucrose, its solubility is not good. Therefore, it is necessary to develop a new sweetener composition with good taste that can achieve similar taste and flavor to sucrose and can be accepted by general consumers. In addition, existing sweetener compositions are prepared by compounding pure raw materials. Such a method requires high purity of raw materials, and the raw materials have to be purified before compounding, thus resulting in high cost. Therefore, a method for producing a low-cost sweetener composition is required.

The present invention solves these long standing challenges. The technical problem to be solved by the present invention is to provide a sweetener composition with good and improved taste. The present disclosure provides an improved biocatalytic process for the preparation of a composition comprising a target steviol glycoside from a starting composition comprising a steviol glycoside substrate, wherein the target steviol glycoside comprises one or more additional glucose units than the steviol glycoside substrate. The sweetener composition comprises rebaudioside D and rebaudioside M at a ratio of rebaudioside D rebaudioside M of 1.5-9:1 by weight. The sweetener can be synthesized by whole cell catalysis, and obtained by catalyzing a substrate to react in the presence of sucrose, zinc chloride and trisodium citrate using rebaudioside A as the substrate and a recombinant microorganism as a catalyst. The method of whole cell catalytic transformation adopted in the invention is simple, and transformation conditions can be controlled to obtain a composition of RD and RM with a specific ratio and low production cost. The composition can effectively solve the problems of taste and flavor of sweeteners, so that the composition is similar to sucrose. In addition, the composition does not introduce any synthetic component, maintains natural features of rebaudioside, does not introduce any energy component, and has the characteristics of no energy (e.g., no calories).

The invention features a particular catalyst, simple method and transformation rate above 90%. No additional UDP or UDPG is needed, contributing to low production cost. The product obtained from biotransformation through the method in the invention is rebaudioside D or rebaudioside M or a mixture thereof, instead of other structures, which facilitates separation and purification in the later stage.

Due to the advantages of high sweetness (250-300 times sweeter than sucrose), low calorie (1/300 of sucrose), no toxic or side effect, no carcinogen and edible safety, steviol glycosides have been widely recognized in many fields such as science and industry. Internationally known as the "third sugar resource around the globe", steviol glycosides have become the third natural substitute for sucrose with development and health value following saccharose and beet sugar.

Steviol Glycosides

Steviol glycosides are a class of sweetener compounds found in the leaves of *Stevia rebaudiana*, a perennial shrub of the Asteraceae (Compositae) family. They are characterized structurally by a single base, steviol, differing by the presence of carbohydrate residues at positions C13 and C19. They accumulate in *Stevia* leaves, composing approximately 10%-20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%).

Stevioside compounds contain a range of components, all of which have tetracyclic diterpene parent nucleuses, different glycosylation modification and different degrees of sweet tastes. Stevioside compounds that have been currently recognized mainly include stevioside (STv), rebaudioside A (RA), rebaudioside C (RC), rebaudioside D (RD), rebaudioside M (RM), etc. For now, only stevioside and RA are commercially applied to food processing fields, including beverages, foods, condiment, alcohol, and dairy products. But their taste is not comparable to sucrose due to the bitterness coming after sweetness. In addition, rather small amount of RD and RM with favorable taste exist in plants, so extraction merely from the leaves of *Stevia rebaudiana* is not adequate for the production; the price is rather high and the market needs cannot be satisfied. In respect of molecular structure, RD contains one more glucose residue than RA, while RM contains one more glucose residue than RD. Therefore, the present invention provides methods of preparing RD or RM with the relative low-cost RA through chemical or biological synthesis.

Rebaudioside D (CAS No: 63279-13-0) is one of the sweet glycosides found in *Stevia rebaudiana*. Its isolation and purification is a very challenging task due to its low content in *Stevia* leaves. The average Rebaudioside D content in dry leaves ranges from about 0.01-0.20%. Moreover, many analytical techniques often fail to detect Rebaudioside D in *Stevia* leaves or steviol glycoside preparations, due to its low content.

Highly purified forms of Rebaudioside D possess a very desirable taste profile, almost lacking in bitterness and in the lingering licorice aftertaste typical for other steviol glycosides. These properties multiply the significance of Rebaudioside D and attract great interest for methods of preparation of highly purified forms of Rebaudioside D.

Sakamoto et al. describe a process of isolation of rebaudioside D from the glycosidic fraction of *Stevia* leave methanolic extract prepared according to Kohda et al. Sakamoto I., Yamasaki Tanaka O. (1977), "Application of $^{13}C$ NMR Spectroscopy to Chemistry of Natural Glycosides: Rebaudioside-C, a New Sweet Diterpene Glycoside of *Stevia rebaudiana*." Chem. Pharm. Bull., 25(4), p. 844; Kohda H., Kasai R., Yamasaki K., Murakami K., Tanaka O. (1976), "New sweet diterpene glucosides from *Stevia rebaudiana*." Phytochemisty, 15, p. 981. The process comprises recrystallization of a glycosidic fraction from methanol and further chromatography on silica gel. The described process employs solvent extraction and chromatographic techniques which are useful in laboratory and pilot scale, but have limited scale-up potential due to the high cost of the rebaudioside Rebaudioside M (CAS No. 1220616-44-3), is a glycoside of steviol, and is identified as 13 [(O-β-D-glucopyranosyl-(1-2)-O-[β-D-glucosylpyranosyl-(1-3)]-β-Dglucosylpyranosyl)oxy]-kaur-16-en-18-oic acid (4-I-O-β-D-glucosylpyranosyl-(1-2)-O[β-D-glucosylpyranosyl-(1-3)]-β-D-glycosylpyranosyl ester. Rebaudioside M is one of a group of known steviol glycosides (SGs) that differ from each other by the number of glycoside moieties and bonding order.

The general structural formula of steviol glycosides are shown in Formula 1. Detailed structures and properties of the specific steviol glycosides STv, RA, RD and RM are provided in Table 1.

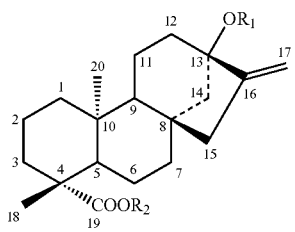

Formula 1 solvent. Yet another example of a starting composition is a commercially available mixture of steviol glycosides brought into solution with a solvent. Other suitable starting compositions include by-products of processes to isolate and purify steviol glycosides.

As used herein, "starting composition" refers to any composition (generally an aqueous solution) containing one or more steviol glycosides, where the one or more steviol glycosides serve as the substrate for the biotransformation.

In some embodiments, the starting composition comprises one or more steviol glycosides selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside X, rebaudioside D, rebaudioside N, rebaudioside O or a synthetic steviol glycoside. In some embodiments, the starting composition comprises rebaudioside A.

In another embodiment, the present invention is a biocatalytic process for the production of reb D from reb A, where the starting composition comprises the steviol glycoside substrate reb A. In a particular embodiment, the present invention is a biocatalytic process for the production of reb D from reb A, where the starting composition comprises partially purified reb A. In another particular embodiment, the present invention is a biocatalytic process for the production of reb D from reb A, where the starting composition comprises purified reb A.

In a particular embodiment, the target steviol glycoside is present in a mixture. For example, in one embodiment, the target steviol glycoside is reb M present in a mixture. In one

TABLE 1

| Description | STv | RA | RD | RM |
|---|---|---|---|---|
| CAS No. | 57817-89-7 | 58543-16-1 | 63279-13-0 | 1220616-44-3 |
| Molecular Weight (g/mol) | 804.87 | 967.01 | 1129.15 | 1291.29 |
| Chemical Formula | $C_{38}H_{60}O_{18}$ | $C_{44}H_{70}O_{23}$ | $C_{50}H_{80}O_{28}$ | $C_{56}H_{90}O_{33}$ |
| R1 | -Gluc-Gluc | —Gluc—Gluc<br>\|<br>Gluc | —Gluc—Gluc<br>\|<br>Gluc | —Gluc—Gluc<br>\|<br>Gluc |
| R2 | -Gluc | -Gluc | -Gluc-Gluc | —Gluc—Gluc<br>\|<br>Gluc |
| Sweetness Multiple (1 for sucrose of the same weight) | 270-300 | 350-450 | 150-250 | 200-350 |

Note:
-Gluc refers to glucose residue.

The term "and/or" used in the invention is to describe combinations of one of any choice. For example, "x, y and/or z" can refer to "x", "y", "z", "x, y and z", "x and y", "x and z" or "y and z". In some embodiments, producing RD and/or RM refers to producing RD, producing RM or producing a mixture of RD and RM.

Starting Compositions

The starting composition may be synthetic or purified (partially or entirely), commercially available or prepared. One example of a starting composition useful in the method of the present invention is an extract obtained from purification of *Stevia rebaudiana* plant material (e.g. leaves). Another example of a starting composition is a commercially available *Stevia* extract brought into solution with a embodiment, the purity of the target steviol glycoside is increased relative to the purity of the target steviol glycoside present in the starting composition. For example, the purity of reb M present in the starting composition is increased as a result of carrying out the method of the present invention.

Optionally, the method of the present invention further comprises separating the target steviol glycoside from the starting composition. The target steviol glycoside can be separated by any suitable method, such as, for example, crystallization, separation by membranes, centrifugation, extraction, chromatographic separation or a combination of such methods.

In some embodiments, the starting composition comprises a purified steviol glycoside substrate. For example, the starting composition may comprise greater than about 90%, 91%, 92%, 93%, 94%, 95%, 96%, 97%, 98% or 99% of a particular substrate steviol glycoside by weight on a dry basis.

In some embodiments, the starting composition comprises a partially purified substrate steviol glycoside composition. For example, the starting composition contains greater than about 50%, about 60%, about 70%, about 80% or about 90% of a particular substrate steviol glycoside by weight on a dry basis.

In another embodiment, the starting composition comprises purified rebaudioside A. In a particular embodiment, the starting composition contains greater than about 99% rebaudioside A by weight on a dry basis. In another embodiment, the starting composition comprises partially purified rebaudioside A. In a particular embodiment, the starting composition contains greater than about 50%, about 60%, about 70%, about 80% or about 90% rebaudioside A by weight on a dry basis.

In one embodiment, the starting composition comprises purified stevioside. In a particular embodiment, the starting composition contains >99% stevioside by weight on a dry basis. In another embodiment, the starting composition comprises partially purified stevioside. In a particular embodiment, the starting composition contains greater than about 50%, about 60%, about 70%, about 80% or about 90% stevioside by weight on a dry basis.

The steviol glycoside component(s) of the starting composition serve as a substrate(s) for the production of the target steviol glycoside(s) (e.g., reb D and/or reb M), as described herein. The target steviol glycoside target(s) differs chemically from its corresponding steviol glycoside substrate(s) by the addition of one or more glucose units.

In some embodiments, the biocatalytic method of the present invention is carried out more than one time, such that the target steviol glycoside produced by a first biocatalytic process serves as the steviol glycoside substrate (which could also be considered an intermediate target steviol glycoside) for a second biocatalytic process in which the target steviol glycoside is produced. In some embodiments, the first substrate is reb A and the second substrate is reb D. In some embodiments, reb D is purified prior to biotransformation to reb M. In some embodiments, reb D is not purified prior biotransformation to reb M.

In some embodiments, reb A is transformed to a mixture of reb D and reb M.

In a particular embodiment, the present invention provides a biocatalytic process for preparing a composition comprising a target steviol glycoside by contacting a starting composition comprising a steviol glycoside substrate with a UDP-glucosyltransferase, thereby producing a composition comprising an intermediate target steviol glycoside comprising one or more additional glucose units than the steviol glycoside substrate; contacting the composition comprising the intermediate target steviol glycoside with UDP-glucosyltransferase, thereby producing a target steviol glycoside comprising one or more additional glucose units than the intermediate target steviol glycoside. Depending on the number of times the method is carried out, there may be one or more intermediate target steviol glycosides (e.g., a first intermediate target steviol glycoside, a second intermediate target steviol glycoside, a third intermediate target steviol glycoside) involved in the production of the target steviol glycoside.

Preparation of Steviol Glycosides

As described herein, genetically engineered bacterium and yeast cells can be used to prepare steviol glycoside compounds and enzymes necessary for the biocatalysis process described herein. A genetically engineered bacterium can be used for producing glycosyltransferase UGT76G1 of *Stevia rebaudiana* (See Chinese Patent Application CN102559528A; herein incorporated by reference). The recombinant genetically engineered bacterium is mainly used for RA production, and unlike the products of the present invention. RA transformed from stevioside through whole-cell catalysis is different from RD or RM prepared according to the invention.

UDP-Glucotransferase

The present method is biocatalytic, i.e., utilizes a biological catalyst. In some embodiments, the biocatalyst is protein enzyme. In a particular embodiment, the biocatalyst is a UDP-glucosyltransferase. The UDP-glucosyltransferase can be any UDP-glucosyltransferase capable of adding at least one glucose unit to the steviol glycoside substrate to provide the target steviol glycoside (e.g., reb D and/or reb M).

In one embodiment, the UDP-glucosyltransferase is produced in a host, such as a microorganism. For example, a DNA sequence encoding UDP-glucosyltransferase is cloned into an expression vector and transferred into a production host such as a microbe, e.g., a bacteria or yeast cell. Non-limiting examples of suitable hosts include *E. coli*, *Saccharomyces* sp., *Aspergillus* sp., *Pichia* sp. The overexpressed protein can be isolated from the cell extract based on its physical and chemical properties, using techniques known in the art. Representative non-limiting techniques for isolating UDP-glucosyltransferase from a host include centrifugation, electrophoresis, liquid chromatography, ion exchange chromatography, gel filtration chromatography or affinity chromatography. In some embodiments, the UDP-glucosyltransferase is not separated from the host microorganism.

UDP-glucosyltransferase may be provided as a whole-cell, crude, semi-purified and purified enzyme preparation(s). In some embodiments, the UDP-glucosyltransferase is provided as a whole-cell mixture.

In some embodiments, the UDP-glucosyltransferase is free. In another embodiment, the UDP-glucosyltransferase is immobilized. For example, UDP-glucosyltransferase may be immobilized to a solid support made from inorganic or organic materials. Non-limiting examples of solid supports suitable to immobilize UDP-glucosyltransferase include derivatized cellulose or glass, ceramics, metal oxides or membranes. UDP-glucosyltransferase may be immobilized to the solid support, for example, by covalent attachment, adsorption, cross-linking, entrapment or encapsulation.

In some embodiments, the UDP-glucosyltransferase is provided in the form of a whole cell system, such as a living microbial cell. The whole cell system may optionally be immobilized, as well, utilizing the techniques identified above with respect to immobilization of the enzyme.

In some embodiments, the UDP-glucosyltransferase is any UDP-glucosyltransferase capable of adding at least one glucose unit to stevioside, thereby producing rebaudioside A. In some embodiments, the UDP-glucosyltransferase is any UDP-glucosyltransferase capable of adding at least one glucose unit to reb A, thereby producing reb D. In some embodiments, the UDP-glucosyltransferase is any UDP-glucosyltransferase capable of adding at least one glucose unit to reb A, thereby producing reb M.

In some embodiments, the UDP-glucosyltransferase is UGT76G1. In some embodiments, the UDP-glucosyltransferase is EUGT11. In some embodiments, the method comprises biotransformation using two or more glucosyltransferase enzymes as catalysts. In some embodiments, the method comprises biotransformation using EUGT11 and UGT76G1.

In some embodiments, the UDP glucosyltransferase comprises EUGT11. In some embodiments, the catalyst used for the biotransformation is performed using an enzyme capable of 1,2-19-O-glucose glycosylation activity. In some embodiments, the UDP glucosyltransferase comprises an enzyme with catalytic activity similar to Accession No. AK121682.1 (*Oryza sativa Japonica* Group).

In some embodiments, the UDP-glucosyltransferase comprises a sequence that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to a sequence provided in Table 13.

The Conversion of Reb A to Reb D

Rebaudioside D (CAS No. 63279-13-0), a glycoside of steviol, is identified as 13-[(2O-β-D-glucopyranosyl-3-O-β-D-glucopyranosyl-β-D-glucopyranosyl)oxy]kaur-16-en18-oic acid, 2-O-β-D-glucopyranosyl-3-O-β-D-glucopyranosyl-β-D-glucopyranosyl ester. Rebaudioside D is one of a group of known steviol glycosides (SGs), which differ from each other by the number of glycoside moieties and bonding order.

In some embodiments, a purified reb D composition is obtained. The manufacturing process of reb D may start with the production of a purified extract of *S. rebaudiana* (*Stevia*). Stevia leaves are extracted in hot water, filtered, and concentrated. The extract is subjected to an adsorption resin that is then eluted with methanol. The eluate is deionized using an ion exchange resin, concentrated, and dried. The dried extract is dissolved in aqueous ethanol, filtered, and crystallized. The crystals are separated, rinsed with ethanol, and recrystallized. Sichuan Ingia states that the resulting product is ≥95% rebaudioside A. Next, a non-pathogenic and non-toxicogenic strain of *Pichia pastoris* (derived from *P. pastoris* ATCC 20864) expressing a uridine-L-diphospho(UDP) glucosyltransferase is used to catalyze the conversion of rebaudioside A to rebaudioside D. The *P. pastoris* strain is grown in culture medium and the cells harvested by filtration. The cells are suspended in a buffer and combined with the rebaudioside A extract and the reaction allowed to proceed. The resultant mixture is centrifuged and the supernatant may be heated to denature any residual enzyme and kill any remaining yeast cells. The supernatant is filtered and subjected to an adsorption resin that is then eluted with ethanol. The eluate is concentrated by evaporation and cooled to crystallize. The wet crystals are washed, dissolved in ethanol, treated with activated charcoal, and rebaudioside D is recrystallized and dried.

Rebaudioside D compositions according to the present invention comprise the following specifications: rebaudioside D (≥95%). In some embodiments, the reb M composition comprises limits for total ash, loss on drying, lead, arsenic, mercury, cadmium, methanol, ethanol, and microorganism content. In some embodiments, the reb D composition comprises total ash (≤1%), loss on drying (≤6%), lead (≤0.05 mg/kg), arsenic (≤0.05 mg/kg), mercury (≤0.05 mg/kg), cadmium (≤0.05 mg/kg), methanol (≤200 mg/kg), ethanol (≤1000 mg/kg), and microorganism content.

In one embodiment, a starting composition comprising reb A is contacted with a UDP-glucosyltransferase capable of catalyzing the reaction of UDP-glucose and reb A to produce reb D. Chemically, a glucose unit is added to the monosaccharide at the C19 position of reb A to provide reb D. In one embodiment, the starting composition comprises partially purified reb A. In another embodiment, the starting composition comprises purified reb A. In a particular embodiment, the starting composition comprises >99% reb A. In a particular embodiment, the starting composition comprises greater than about 50%, about 60%, about 70% about 80% or about 90% reb A.

In a particular embodiment, the UDP-glucosyltransferase is UGT91D2, which has been described by Joseph et al. (Genbank accession no. ACE87855). It has to be noted that similar sequence was described later in a patent application PCT/US2011/038967 and named UGT91D2e. UGT91D2e shares >95% identity with UGT91D11 (Genbank accession no. AAR06918) and >99% identity with UGT of Joseph et al. (Genbank accession no. ACE87855).

In some embodiments, the UDP-glucosyltransferase, such as UGT91D2, is prepared by expression in a host microorganism. Suitable host microorganisms include, but are not limited to, *E. coli, Saccharomyces* sp., *Aspergillus* sp., *Pichia* sp. In a particular embodiment, UGT91D2 is expressed in *E. coli*.

The UDP-glucosyltransferase, such as UGT91D2, can be provided free or in an immobilized form. The enzyme preparation may be crude, semi-purified and purified. In one embodiment, the UDP-glucosyltransferase is provided as a whole-cell system, e.g., a living microbial cell, or whole microbial cells, cell lysate and/or any other form of known in the art.

The reaction medium for conversion is generally aqueous, and can be purified water, buffer or a combination thereof. In a particular embodiment, the reaction medium is a buffer. Suitable buffers include, but are not limited to, PIPES buffer, acetate buffer and phosphate buffer. In one embodiment, the reaction medium is phosphate buffer.

In one embodiment, conversion of reb A to reb D further comprising the addition of compounds other than UDP-glucose, reb A and the UDP-glucosyltransferase. For example, in some embodiments, the reaction medium includes $MgCl_2$ and/or $MnCl_2$.

The reaction can be carried out at temperature between about 0° C. and about 60° C., such as, for example, about 10° C., about 20° C., about 30° C., about 40° C., about 50° C. or about 60° C. In a particular embodiment, the reaction is carried out at about 30° C.

The reaction can proceed for a duration of time between 1 hour and 1 week, such as, for example, about 6 hours, about 12 hours, about 24 hours, about 48 hours, about 72 hours, about 120 hours, about 3 days, about 4 days, about 5 days, about 6 days or about 7 days. In a particular embodiment, the reaction is carried out for about 120 hours.

Optionally, the UDP-glucose, which is used as glucose donor, can be recycled by the use of the enzyme sucrose synthase. Reb A is transformed into reb D with UDP-glucose which is recycled by the reaction between sucrose and UDP. As a consequence, reb A and sucrose are used in stoichiometric amounts whereas UDP is present in catalytic amounts.

The reaction can be monitored by suitable method including, but not limited to, HPLC, LCMS, TLC, IR or NMR.

In one embodiment, the conversion of reb A to reb D is at least about 2% complete, as determined by any of the methods mentioned above. In a particular embodiment, the conversion of reb A to reb D is at least about 10% complete, at least about 20% complete, at least about 30% complete, at least about 40% complete, at least about 50% complete, at least about 60% complete, at least about 70% complete, at least about 80% complete or at least about 90% complete. In a particular embodiment, the conversion of reb A to reb D is at least about 95% complete.

The Conversion of Reb D to Reb M

The manufacturing process starts with the extraction of *S. rebaudiana* (*Stevia*) leaves with a suitable solvent and then filtered and concentrated. The *Stevia* extract is then subjected to purification steps that include treatment with an adsorption resin, deionization, and recrystallization to obtain an extract containing 95% rebaudioside A. A non-pathogenic and non-toxicogenic strain of *Pichia pastoris* is engineered to express two glucosyltransferases that are used to catalyze the conversion of rebaudioside A to rebaudioside M. The *P. pastoris* strain is grown in culture and the cells may be harvested by filtration. The cells are suspended in a sodium phosphate buffer and transferred to a reaction tank. The *Stevia* extract is added, and the reaction allowed to proceed until the desired conversion to rebaudioside M is complete. The enzymes and yeast cells are inactivated by heating and removed by filtration. The resulting solution is subjected to an adsorption resin that is then eluted with ethanol. The eluate is concentrated by evaporation, cooled, and then centrifuged. The precipitate is dissolved in ethanol, activated carbon added, and the mixture filtered. Rebaudioside M is crystallized from the resulting solution, collected by centrifugation, and finally dried.

Rebaudioside M compositions according to the present invention comprise the following specifications: total SGs ((≥95%), rebaudioside M (≥95%). In some embodiments, the reb M composition comprises limits for total ash, loss on drying, lead, arsenic, mercury, cadmium, methanol, ethanol, and microorganism content. In some embodiments, the reb M composition comprises total ash (≤1%), loss on drying (≤6%), lead (≤1 mg/kg), arsenic (≤1 mg/kg), mercury (≤1 mg/kg), cadmium (≤1 mg/kg), methanol (≤200 mg/kg), ethanol (≤5000 mg/kg), and microorganism content.

In some embodiment, the starting composition comprises reb D, which is contacted with a UDP-glucosyltransferase capable of catalyzing the reaction of UDP-glucose and reb D to produce reb M. Chemically, a glucose unit is added to the disaccharide at the C19 position of reb D to provide reb M. In one embodiment, the starting composition comprises partially purified reb D. In another embodiment, the starting composition comprises purified reb D. In a particular embodiment, the starting composition comprises >99% reb D. In a particular embodiment, the starting composition comprises greater than about 50%, about 60%, about 70% about 80% or about 90% reb D. In a particular embodiment, the UDP-glucosyltransferase is UGT76G1.

In some embodiments, the UDP-glucosyltransferase, such as UGT91D2, can be prepared by expression in a host microorganism. Suitable host microorganisms include, but are not limited to, *E. coli, Saccharomyces* sp., *Aspergillus* sp., *Pichia* sp. In a particular embodiment, UGT91D2 is expressed in *E. coli.*

The UDP-glucosyltransferase, such as UGT91D2, can be provided as free or immobilized. The enzyme preparation can be crude, semi-purified and purified. In one embodiment, the UDP-glucosyltransferase is provided as a whole cell preparation, e.g., living microbial cells, or in the form of whole microbial cells, cell lysate and/or any other form of known in the art.

The reaction medium for conversion is generally aqueous, and can be purified water, buffer or a combination thereof. In a particular embodiment, the reaction medium is a buffer. Suitable buffers include, but are not limited to, PIPES buffer, acetate buffer and phosphate buffer. In one embodiment, the reaction medium is phosphate buffer.

In one embodiment, conversion of reb D to reb M employs compounds in addition to UDP-glucose, reb D and the UDP-glucosyltransferase. For example, in some embodiments, the reaction medium includes $MgCl_2$ and/or $MnCl_2$.

The reaction can be carried out at temperature between about 0° C. and about 60° C., such as, for example, about 10° C., about 20° C., about 30° C., about 40° C., about 50° C. or about 60° C. In a particular embodiment, the reaction is carried out at about 30° C.

The reaction can proceed for a duration of time between 1 hour and 1 week, such as, for example, about 6 hours, about 12 hours, about 24 hours, about 48 hours, about 72 hours, about 120 hours, about 3 days, about 4 days, about 5 days, about 6 days or about 7 days. In a particular embodiment, the reaction is carried out for about 120 hours.

Optionally, the UDP-glucose, which is used as glucose donor, can be recycled by the use of the enzyme Sucrose Synthase. Reb D is transformed into reb M with UDP-glucose which is recycled by the reaction between sucrose and UDP. As a consequence, reb D and sucrose are used in stoichiometric amounts whereas UDP is present in catalytic amounts.

The reaction can be monitored by suitable method including, but not limited to, HPLC, LCMS, TLC, IR or NMR.

In one embodiment, the conversion of reb D to reb M is at least about 50% complete, as determined by any of the methods mentioned above. In a particular embodiment, the conversion of reb D to reb M is at least about 60% complete, at least about 70% complete, at least about 80% complete or at least about 90% complete. In a particular embodiment, the conversion of reb D to reb M is at least about 95% complete.

The target steviol glycoside is optionally purified from the resulting composition. Purification of the target steviol glycoside from the reaction medium can be achieved by any suitable method to provide a highly purified target steviol glycoside composition. Suitable methods include crystallization, separation by membranes, centrifugation, extraction (liquid or solid phase), chromatographic separation, HPLC (preparative or analytical) or a combination of such methods.

In one embodiment, the particular biocatalytic conversion can be quenched to stop the reaction. The resultant mixture is then centrifuged. The supernatant generally contains the target steviol glycosides, and can then be further purified, if desired. For example, analytical or preparative HPLC can be used to separate remaining target or starting steviol glycoside(s) or reaction by-products from the target steviol glycoside. In one embodiment, separation is achieved with analytical HPLC. In another embodiment, separation is achieved with preparative HPLC. One of skill in the art will recognize that the particular HPLC method used can vary based on the particular system, solvent, and column. A suitable system for separating reb M from reb D is provided in the Example 20.

It is envisaged that the method provided herein can be repeated, wherein the composition resulting from the initial process, i.e., the composition comprising the target steviol glycoside, can then be used as the starting composition when the method is carried out a second time- or optionally, the target steviol glycoside can be purified from the composition comprising the target steviol glycoside to provide a highly purified target steviol glycoside or steviol glycoside composition. According to this embodiment, the target steviol glycoside produced when the method is carried out the first time can be considered a first target steviol glycoside or an intermediate target steviol glycoside, useful as a substrate for the production of a second target steviol glycoside, a second intermediate target steviol glycoside or an ultimate target steviol glycoside. The process can be repeated as many times as required to arrive at the ultimate target steviol glycoside. In one embodiment, the method is repeated once. In another embodiment, the method is repeated twice. In yet another embodiment, the method is repeated three times. In still other embodiments, the method is repeated four, five, six, seven, eight or nine times. On of skill in the art will recognize that the particular UDP-glucosyltransferase used in each reaction can either be the same or different, depending on the particular site on the steviol glycoside substrate where glucose is to be added.

Accordingly, in one embodiment, the method is repeated once, wherein the starting composition of the first method comprises reb A and the target steviol glycoside is reb D, and wherein starting composition of the second method comprises reb D and the target steviol glycoside is reb M.

In another embodiment, the method is repeated twice, wherein the starting composition of the first method comprises stevioside and the target steviol glycoside is reb A; the starting composition of the second method comprises reb A and the target steviol glycoside is reb D; and the starting composition of the third method comprises reb D and the target steviol glycoside is reb M.

In still another embodiment, the method is repeated three times, where the starting composition of the first method comprises rubusoside and the target steviol glycoside is stevioside; the starting composition of the second method comprises stevioside and the target steviol glycoside is reb A; the starting composition of the third method comprises reb A and the target steviol glycoside is reb D; and the starting composition of the fourth method comprises reb D and the target steviol glycoside is reb M.

Other properties of the pure reb M compound include a melting point of 249-250° C., and a specific rotation of $[\alpha]D$ 25-19.0° in 50% ethanol (C=1.0). The solubility of reb M in water is around 0.3%, and increases with an increase in temperature.

Reb M is soluble in diluted solutions of methanol, ethanol, n-propanol, and isopropanol. However, it is insoluble in acetone, benzene, chloroform, and ether.

Reb M obtained in accordance with the present invention is heat and pH-stable.

Highly purified target glycoside(s) particularly, reb D and/or reb M obtained according to this invention can be used "as-is" or in combination with other sweeteners, flavors and food ingredients.

Non-limiting examples of flavors include lime, lemon, orange, fruit, banana, grape, pear, pineapple, mango, bitter almond, cola, cinnamon, sugar, cotton candy and vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners and gelling agents.

Highly purified target glycoside(s) particularly, reb D and/or reb M obtained according to this invention can be prepared in various polymorphic forms, including but not limited to hydrates, solvates, anhydrous, amorphous forms and/or mixtures thereof.

Highly purified target steviol glycoside(s), particularly, reb D and/or reb M obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

Highly purified target steviol glycoside(s), particularly, reb D and/or reb M as a sweetening compound may be employed as the sole sweetener, or it may be used together with other naturally occurring high intensity sweeteners such as stevioside, reb A, reb B, reb C, reb D, reb E, reb F, steviolbioside, dulcoside A, rubusoside, mogrosides, brazzein, neohesperidin dihydrochalcone, glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, mogroside V, siamenoside and others.

Highly purified target steviol glycoside(s), particularly, reb D and/or reb M may also be used in combination with synthetic high intensity sweeteners such as sucralose, potassium acesulfame, aspartame, alitame, saccharin, neohesperidin dihydrochalcone, cyclamate, neotame, dulcin, suosan, N—[—N-[3-(3-hydroxy-4-methoxyphenyl)propyl]-L-α-aspartyl]-L-phenylalanine 1-methyl ester, N—[—N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

Moreover, highly purified target steviol glycoside(s), particularly, reb D and/or reb M can be used in combination with natural sweetener suppressors such as gymnemic acid, hodulcin, ziziphin, lactisole, and others. Reb D and/or reb M may also be combined with various umami taste enhancers. Reb D and/or reb M can be mixed with umami tasting and sweet aminoacids such as glutamate, aspartic acid, glycine, alanine, threonine, proline, serine, glutamate, and tryptophan.

Highly purified target steviol glycoside(s), particularly, reb D and/or reb M may also be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Highly purified target steviol glycoside(s), particularly, reb D and/or reb M may be combined with reduced calorie sweeteners such as D-tagatose, L-sugars, L-sorbose, L-arabinose, and others.

Steviol glycoside may be prepared using a fermentation method at high pH and a mixture obtained thereby (See Chinese Patent Application CN107949632A which is hereby incorporated by reference).

Methods for improving preparation of RD and RM using recombinant cells to lengthen the stevioside and its mixture are described in Chinese Patent Application CN105051195A, which is hereby incorporated by reference. A mixture of a plurality of steviosides will be produced through the method, and separation and purification in the later stage costs high.

As described in Chinese Patent Application CN106834389A, recombinant bacteria can be used to catalyze RA by a method for preparing rebaudioside M2 (RM2). After inducible expression of recombinant bacteria of glycosyltransferase (EUGT11) with tomato source and synthetase (StSUS) with potato source, crude enzyme is added to the reaction system to catalyze the generation of RM2 from RA. The RM2 prepared through the method is an isomer of RM instead of Stevia rebaudiana extract. It can be obtained only by chemical synthesis instead of extraction from natural substances. Since its safety is unknown and it has no GRAS (Generally Recognized as safe) certificate issued by FDA, it cannot be sold as a legal food additive for sale. The RD and RM in the invention have been certified by GRAS and released to the market for sale, with promising prospect.

Methods for preparing RM through enzymes are described in Chinese Patent Application CN103757074A. The method comprises using RA or RD as the substrate and, in the presence of sucrose and UDPG, recombinant cell or an enzyme expressed by the relevant recombinant cell as the catalyst to generate RM through transformation. However, the method needs additional high-priced UDPG, which means higher cost. In addition, use of recombinant cell as the catalyst in the method results in relatively low transformation rate of RA, merely above 40%. Further improvement is necessary.

A method for preparing RM by Pichia pastoris with enzymes are described in Patent CN105200098A, which is hereby incorporated by reference. The method comprises using recombinant Pichia pastoris with UDP-glucosyltransferase or UDP-glucosyltransferase prepared thereby to catalyze the generation of RM from RA or RD in the co-presence of glucosyl group. In the method, recombinant cell is used as the catalyst and the transformation rate of RA is above 40% during whole-cell transformation.

The method for producing RD and/or RM in the invention comprises the following steps: using RA and/or stevioside as substrate and a recombinant microorganism and/or an enzyme produced by the recombinant microorganism and/or a metabolite of the recombinant microorganism to catalyze the reaction of the substrate in the presence of sucrose and trisodium citrate, producing a mixture of RD and RM, and then separating and purifying the mixture to obtain RD or RM. The recombinant microorganism has encoding genes of EUGT11 and UGT76G1.

1. Catalyst

The invention adopts the method of biotransformation to obtain RD and/or RM. Biotransformation in the invention refers to the process of using enzyme or biological organisms (including cells, organelle and tissues) as the catalyst for chemical transformation. The reaction features mild conditions and efficient substrate selectivity. The key to the reaction is the catalyst.

The catalyst used in the invention is a recombinant microorganism and/or an enzyme produced by the recombinant microorganism and/or a metabolite of the recombinant microorganism. Introduction to recombinant microorganism is detailed as follows:

The recombinant microorganism used in the invention contains encoding genes of glycosyltransferase EUGT11 and UGT76G1. The original sequences are all from NCBI Database. Wherein, the EUGT11 gene (No. AK121682.1) is from oryzasativa and the UGT76G1 gene (No. AY345974) is from Stevia rebaudiana.

In the invention, RD or RM can be obtained from RA through glycosyl transfer in the presence of uridine diphosphate glucose (UDPG). During metabolism, the microorganism can produce UDPG of rather low concentration that can only meet the need of metabolism of the bacteria. Therefore, proper concentration of UDPG in the catalysis system is necessary for higher production and transformation rate. One method is to add additional UDPG to the catalysis system. But the UDPG is expensive and exogenous addition can significantly increase the cost. Therefore, the invention has made modifications to the recombinant microorganism. On one hand, the metabolic flux of the host is modified, pgm gene, glgC gene and agp gene are knocked out, the metabolite is guided to move along the UDPG gathering direction, and the UDPG consumption is decreased; On the other hand, the UDPG synthesis pathways of other species in nature are investigated and introduced to the host system, the ushA gene of the recombinant microorganism is replaced with Basp gene and ugpA gene to achieve UDPG gathering and improve transformation rate.

A bioengineering method can be used to construct recombinant microorganism: First, obtaining the EUGT11 encoding gene and UGT76G1 encoding gene, then connecting the target genes to the carrier DNA fragment to obtain the recombinant DNA molecule; next, introducing the recombinant DNA molecule to suitable host cell, and finally selecting the monoclone with target genes to obtain the recombinant microorganism. Common host expressing cells in the art are all applicable to the invention, such as Escherichia coli, saccharomycetes, Bacillus subtilis, Corynebacterium glutamicum or streptomycete. Introduction of EUGT11 encoding gene and UGT76G1 encoding gene into these host cells can generate recombinant Escherichia coli, recombinant saccharomycetes, recombinant Bacillus subtilis, recombinant Corynebacterium glutamicum or recombinant streptomycete.

As one of the embodiments, the recombinant Escherichia coli are used as expression strains. With their short fermentation period, low cost and good catalytic activity, the final transformation rate can be improved. Before the construction of recombinant bacteria, the chassis of Escherichia coli are modified in two steps. First, the phosphoglucomutase (pgm) gene, G1P adenylyl transferase (glgC) gene and G1P phosphatases (agp) gene in the E. coli BL21 (DE3) are knocked out in the G1P non-UDPG synthesis and consumption pathways according to the modified XRed-CRISPR/Cas technique. Second, heterogenous genes, including BasP gene (NCBI Gene ID: 4556453) from Bifidobacterium adolescentis and G1P UgpA gene (NCBI Gene ID: 9889115) from Bifidobacterium bifidum, are introduced into the chromosome. These two genes are integrated on the T5 operon and replace the strain's own UDPG synthetase gene, ushA, so as to obtain E. coli BL21(DE3)ΔglgCΔpgmΔagpΔushΔ:: operon T5 (including BasP and UgpA). The consumption of UDG is thus decreased, and endogenous UDPG gathering is achieved. The UDPG from its own synthesis can meet the transformation need, without the need of additional exogenous UDPG, contributing to low transformation cost and high transformation rate of RD and RM.

Co-expression carrier pETDuet (ampicillin resistant) is used to construct recombinant plasmid. Total RNA of oryzasativa leaves is extracted and cDNA is obtained through reverse transcription. According to EUGT11 gene sequence in the NCBI Database, PCR primer is designed and the restriction enzyme cutting sites, BamHI and HindIII, are introduced respectively at the upstream and downstream. The EUGT11 gene segment is obtained through PCR, and subject to double digestion along with pETDuet plasmid respectively with BamHI and HindIII, and then connected with connection enzyme T4 to obtain pETDuet-EUGT11 recombinant plasmid. The E. coli Top 10 competent cells are transformed through heat shock of calcium chloride and plasmid is obtained through propagation.

The UGT76G1 segment is obtained through the same method: According to UGT76G1 gene sequence in the NCBI Database, PCR primer is designed and the restriction enzyme cutting sites, NcoI and SpeI, are introduced respectively at the upstream and downstream. The UGT76G1 gene segment is obtained through PCR, and subject to double digestion along with pETDuet-EUGT11 plasmid respectively with NcoI and SpeI, and then connected to obtain co-expression plasmid pETDuet-EUGT11-UGT76G1. The unmodified E. coli BL21 (DE3) and E. coli BL21(DE3) ΔglgCΔpgmΔagpΔushΔ::operon T5 (including BasP and UgpA) competent cells are respectively transformed. Positive clone is selected through resistance screening and breed conservation is conducted for fermentation and transformation.

Wherein, relevant genes and sequences are shown in Table 2.

As another embodiment, the recombinant microorganism is recombinant Pichia pastoris, preferably Pichia pastoris GS115. The pgm gene, glgC gene and agp gene in the genome are knocked out according to the method of CRISPR-Cas9 to obtain GS115ΔglgCΔpgmΔagpΔushΔ.

Yeast expression carrier pPICZA (bleomycin resistant) is used to construct recombinant plasmid. PCR primer is respectively designed. The restriction enzyme cutting sites, EcoRI and KpnI, are introduced respectively at the two ends of the EUGT11 and UGT76G1 gene segments and connected to pPICZA plasmid after digestion to construct pPICZA-EUGT11 and pPICZA-UGT76G1 recombinant plasmid. Then, primer is designed according to sequence of AOX1 promoter on pPICZA, the restriction enzyme cutting sites, XhoI and NotI, are introduced and PCR is conducted with the pPICZA-UGT76G1 as template to obtain complete expression sequence module. Double digestion is conducted to PCR product and pPICZA-EUGT11 recombinant plasmid respectively with XhoI and NotI. The product is recovered and connected to construct pPICZA-EUGT11-UGT76G1 co-expression carrier and transformed into the unmodified Pichia pastoris GS115 and GS115ΔglgCΔpgmΔagpΔushΔ competent cells through electric shock. Positive clone is selected through resistance screening and breed conservation is conducted for fermentation and transformation.

2. Catalytic Reaction

As an embodiment, the invention comprises using whole cell of a recombinant microorganism and/or a crude enzyme produced by the recombinant microorganism to catalyze the substrate for reaction. The crude enzyme contains glucosyltransferase produced by the recombinant microorganism and some secondary metabolites, UDP.

Preferably, in the catalysis and transformation system, the concentration of whole cell and/or crude enzyme is 5%-30% by wet weight (w/v), that of substrate is 1-100 g/L; that of trisodium citrate is 50-80 mM, that of sucrose is 30-90% (w/v), and the pH is 7-8.

Concentration of Whole Cell and/or Crude Enzyme

The whole cell and/or crude enzyme can be used for enzyme catalysis. Crude enzyme refers to the enzyme solution at the preliminary enzyme extraction of tissue or genetically engineered bacterium and before further purification and refinement. The crude enzyme in the invention contains glucosyltransferase produced by the recombinant microorganism and some secondary metabolites, UDP. The concentration of whole cell and/or crude enzyme is calculated by wet weight (unit: w/v), i.e., the weight of whole cell and/or crude enzyme per unit volume. The concentration of whole cell and/or crude enzyme has certain influence on catalysis. Within certain limits, the content of enzyme in the reaction system and the reaction rate increase as the concentration increase of whole cell and/or crude enzyme. Thus, higher transformation rate is achieved within the same time.

TABLE 2

| Gene Name | Sequence | SEQ ID NO: |
|---|---|---|
| EUGT11 gene | NCBI No. AK121682.1 | 1 |
| UGT76G1 gene | NCBI No. AY345974.1 | 4 |
| pgm gene | gRNA: gcagccgttc gtggaagggc caatgacttg ggtcgtaagc acctgcattt atttccgttc | 11 |
| glgC gene | gRNA: cgatcgtaca tatccagctc ttgttaccgg aagtatgggt tgtagatatg gtcgcccgcc | 12 |
| agp gene | gRNA: agaaaccgtt ggcatctatc gcatatacgg tgtccggcgg ttgttgatac ttcgcgctaa | 13 |
| ushA gene | gRNA: ctcgcttttc ccgtcttccc ttgtacagac caatatgggg accaattttt gctgtgtcat | 14 |
| BasP gene | NCBI Gene ID: 4556453 | 15 |
| UgpA gene | NCBI Gene ID: 9889115 | 17 |

However, the concentration of whole cell and/or crude enzyme exceeding a certain level will change the viscosity of reaction liquid, the substrate, the resolution status of product and the buffer ability of buffer solution and influence and the status of mass transfer, further influence the transformation effect. In addition, excessive consumption of whole cell and/or crude enzyme is not contributable to cost control. Preferably, the concentration of whole cell and/or crude enzyme is 5-30%.

2.2 Concentration of Substrate

According to the method of the invention, RA and/or STv can be used as the substrate. In some embodiments, RA is the substrate. In some embodiments STv is the substrate.

RA is a kind of commercially available material of relatively high purity, for example, purity >80% RA, purity >95% RA, or purity ≥97% RA. Preferably, the purity is ≥97% RA. RA is usually purified by solvent recrystallization, resin absorption or chromatography and fractionation to decrease the content of other impurities.

STv is also a kind of commercially available material of relatively high purity that can be directly purchased.

Concentration of substrate influences the transformation rate and the concentration of product. Preferably, the concentration of substrate is 1-100 g/L. In some embodiments, the concentration of substrate is 1 g/L, 3 g/L, 10 g/L, 20 g/L, 30 g/L, 40 g/L, 50 g/L, 60 g/L, 70 g/, 80 g/L, 90 g/L or 100 g/L.

Trisodium Citrate

Trisodium citrate, also known as sodium citrate, is a common industrial chemical reagent. Trisodium citrate inhibits glycolytic pathway and promotes the generation of UDPG. Therefore, it can be added into the catalysis system of the invention to promote the reaction.

The preferred concentration of trisodium citrate in the invention is 50-80 mM. Specifically, in some embodiments, the concentration of trisodium citrate is 50 mM, 60 mM, 65 mM, 70 mM, 75 mM or 80 mM.

Sucrose

In the method of the invention, the sucrose is the common disaccharide. The concentration of sucrose in the invention is indicated as the weight to volume ratio (w/v), i.e., the weight of sucrose in the reaction system to the volume of the entire system ratio. It is found through the study that the concentration of sucrose has significant influence on the transformation rate. Low concentration of sucrose will cause incomplete operation of the UDPG synthesis mechanism and inadequate UDPG supply, further influence the transformation rate. It is also found through microscope examination that concentration of sucrose ≥40% will cause massive disruption of microorganisms in the transformation system, so that crude enzyme will be released into the system.

Therefore, the preferred concentration of sucrose is 30-90%. In some embodiments, the preferred range of concentration of sucrose of 30-40%. In some embodiments, the preferred concentration of sucrose is in the range of 40-90%. Specifically, in some embodiments, the concentration of sucrose is 30%, 35%, 38%, 39%, 40%, 41%, 42%, 45%, 50%, 55%, 60%, 65%, 70%, 75%, 80%, 85% or 90%.

System pH

The pH of enzymatic reaction system is the key to catalytic reaction. The invention is embodied in an aqueous system, so the pH is required to be 6-9. It is found in the study that, at appropriate pH, the catalysis efficiency is stable and the transformation rate is high, while at a higher or lower pH than the appropriate value, the dissociation of genes at active sites of the enzyme is not conducive to the combination of the enzyme and the substrate, and the activity of the enzyme will also decrease accordingly. In addition to influence on catalysis efficiency, the pH is also relevant to the stability of UDPG. As a pyrophosphate compound, UDPG shows favorable stability under mild alkaline conditions.

Therefore, the preferred pH in the invention is 7-8. In some embodiments, the preferred pH is 7 or 7.1-8. Specifically, in some embodiments, the pH is 7, 7.3, 7.5, 7.6, 7.7, 7.8, 7.9 or 8.0.

As a preferred embodiment, the concentration of whole cell and/or crude enzyme is 15%, that of substrate is 30 g/L; that of trisodium citrate is 60 mM, that of sucrose is 50% (w/v), and the pH is 7.3. Under such catalysis and transformation conditions, the catalytic efficiency is highest and the transformation rate of substrate also increases accordingly.

Reaction Temperature

Reaction temperature influences production of RD and/or RM. The temperature not only relates to the activity of enzyme but also influences the molecular movement of substrate and donor. Excessive reaction temperature has adverse effect on the stability of enzyme, which may cause structural damage to protein and even degeneration into non-functional precipitation. The recombinant microorganism and produced enzyme may be inactivated, resulting in decreased catalysis activity and consequently influencing the synthesis of product. However, at low reaction temperature, the recombinant microorganism of low activity produces small amount of enzyme, the Brownian Motion of molecules is relatively weak, and the catalysis activity of the metabolite is not strong, thus influencing the transformation rate of substrate. Therefore, the preferred reaction temperature is 35-42° C. Specifically, in some embodiments, the reaction temperature is 35° C., 36° C., 37° C., 38° C., 39° C., 40° C., 41° C. or 42° C.

Reaction Time

Reaction time has influence on the transformation rate from substrate to RD and/or RM. Short reaction time causes incomplete reaction and low transformation rate. Therefore, to achieve complete reaction, the preferred reaction time in the invention is above 10 h. Transformation rate increases as the reaction time extends within limited range. When the transformation rate reaches a certain level and the substrate is completely transformed, further extension of reaction time will no longer deliver positive effect but can decrease the production efficiency. Preferably, the reaction time can be 10-240 h.

In some embodiments, the reaction temperature is 35° C., the reaction time is 40-240 h, the preferred reaction temperature is 35° C. and reaction time is 240 h. In some embodiments, the reaction temperature is 36° C., the reaction time is 30-240 h, the preferred reaction temperature is 36° C. and reaction time is 200 h. In some embodiments, the reaction temperature is 37° C., the reaction time is 24-240 h, the preferred reaction temperature is 37° C. and reaction time is 160 h. In some embodiments, the reaction temperature is 38° C., the reaction time is 22-240 h, the preferred reaction temperature is 38° C. and reaction time is 140 h. In some embodiments, the reaction temperature is 39° C., the reaction time is 21-240 h, the preferred reaction temperature is 39° C. and reaction time is 120 h. In some embodiments, the reaction temperature is 40° C., the reaction time is 20-240 h, the preferred reaction temperature is 40° C., and reaction time is 120 h.

In addition, the invention can also purify crude enzyme and use the purified product to catalyze the reaction as a catalyst. Through methods in the art, such separation and purification methods as solution recrystallization, resin absorption or chromatography and fractionation, enzyme can be extracted from the metabolite to be directly used for catalysis and transformation. However, in such case, the enzyme extraction process will be increased, followed by higher production cost.

In the reaction system of the invention, hypertonic sucrose system is used as the reaction liquid. The sucrose of high concentration can prevent the structure of enzyme from any change and decrease the risk of bacterial contamination. When the concentration of sucrose is in the range of 30-40%, the bacteria generally show no disruption, indicating whole-cell catalysis reaction. Complete biological organism (i.e., whole cell, tissue and even individual organism) can be used as catalyst for chemical transformation. Essentially, the enzyme in cell is used for catalysis. As another embodiment, the invention can also use sucrose with concentration of 40-90%. The bacteria is disrupted under such condition and the substance in the cell is released into the system to expedite the catalysis rate and, in the meantime, eliminate the need of complicated enzyme purification process, contributing to simpler preparation and lower production cost.

Separation and Purification of Product

The reaction system is a mixture of contents of bacteria, inorganic salt, sucrose, substrate and product. Separation and purification comprise the following steps:

a. Heating, macro-filtering and ultra-filtering the reaction liquid containing a mixture of rebaudioside D and rebaudioside M for removal of the denatured protein and other insoluble substances precipitated in the reaction system. Macro-filtration is usually carried out with frame filtration. After macro-filtration, ultra-filtration is carried out for removal of soluble protein, macromolecular pigment and other macromolecular substances in the reaction liquid and for collection of the ultrafiltrate. The ultrafiltrate mainly comprises the reaction substrate and product, as well as salt, sucrose and other micromolecular substances in the reaction system.

b. Separating the ultrafiltrate through nanofiltration to obtain a retentate. The nanofiltrate comprises sucrose, inorganic salt and other micromolecular substances, while the retentate mainly comprises rebaudioside D and/or rebaudioside M.

c. Obtaining highly pure rebaudioside D and/or rebaudioside M by concentrating, crystallizing and drying the retentate; alternatively spray-drying the concentrated retentate to obtain a highly water-soluble mixture of rebaudioside D and/or rebaudioside M.

Membrane filtration refers to the process that a filtration membrane of certain pore size is used to filtrate the solution containing macromolecule or fine particles and separate such macromolecule or fine particles from the solution. Driven by pressure difference between two sides of the filtration membrane, the filtration membrane is used as filtering medium and, under certain pressure, micromolecular solute and solvent are allowed to pass the ultrafiltration membrane of certain pore size and retain macromolecular solute on the side of mother liquid, so as to achieve purification, separation and concentration of the solution. Filtration can be divided by the membrane pore size into microfiltration, ultrafiltration, nanofiltration and reverse osmosis.

For ultrafiltration, the membrane pore size is usually 2-100 nm, the retained molecule weight is in the range of 10000-30000. Through ultrafiltration can be efficiently separated the insoluble particles and macromolecules, including protein, phospholipid, polysaccharide and nucleic acid in the solution, allowing the substances such as stevioside, sucrose and inorganic salt in the solution to pass the membrane along with the ultrafiltrate.

Nanofiltration membrane technology is a kind of membrane separation technology between ultrafiltration and reverse osmosis. The retained molecule weight is approximately 200-500 and pore size is 1nm, therefore, it is named as nanofiltration. In the treatment process, sucrose and inorganic salt pass through the membrane and the stevioside with molecule weight of around 1000 is retained for further separation and purification.

EXAMPLES

Example 1: Steviol Glycoside Production Using Recombinant *Escherichia coli*

Total RNA of oryzasativa leaves was extracted and cDNA was obtained by reverse transcription. According to EUGT11 gene sequence (Accession No. AK121682) in the GeneBank Database, a PCR amplification primer was designed and the sites, BamHI and HindIII, were introduced respectively to the primers at the upstream and downstream.

```
F:
                                     (SEQ ID NO: 19)
5'-CGCGGATCCATGGACTCCGGCTACTCCTCC-3'

R:
                                     (SEQ ID NO: 20)
5'-CCCAAGCTTTCAATCCTTGTAAGATCTCAATTGC-3
```

The gene encoding EUGT11 was amplified using PCR amplification. Double digestion with BamHI and HindIII was performed on the EUGT11 PCR amplified and the expression carrier pETDuet, and the target segment is recovered and then connected with connection enzyme to obtain pETDuet-EUGT11.

Total RNA of *Stevia rebaudiana* is extracted and cDNA of *Stevia rebaudiana* is obtained through reverse transcription. According to UGT76G1 gene sequence, PCR amplification primer is designed and the sites, NcoI and SpeI, are introduced respectively to the primer at the upstream and downstream. Forward and reverse primers w

```
UGT76G1 F:
                                     SEQ ID NO: 21
5'-CATGCCATGGAAAACAAAACCGAAACCACCGTT-3'

UGT76G1 R:
                                     SEQ ID NO: 22
5'-GGACTAGTTTAACTAGTCAGAGAAGAGATGTA-3'
```

UGT76G1 encoding gene was obtained through PCR amplification. Double digestion was conducted to the UGT76G1 segment and pETDuet-EUGT11 respectively with NcoI and SpeI, and the target segment was recovered and then connected with connection enzyme to obtain the co-expression plasmid pETDuet-EUGT11-UGT76G1. The unmodified *E. coli* BL21 (DE3) and *E. coli* BL21(DE3) ΔglgCΔpgmΔagpΔushΔ::operon T5 (including BasP and UgpA) competent cells in the chassis were respectively transformed. The expression strain 1 and strain 2 of recombinant *Escherichia coli* were obtained through resistance screening.

2. Bacteria Culture and Protein Expression

Recombinant *Escherichia coli* were selected and inoculated to a 2 ml LB culture medium (small test tube of 20 mL) with 100 μg/mL of ampicillin, and cultured for 4 h at 37° C. Then, 1% of the obtained *Escherichia coli* was inoculated to a 100 mL M9 culture medium (conical flask of 500 mL) and cultured for 2 h at 37° C. and 250 rpm (OD600-0.6), cooled for 10 min with tap water, placed in a temperature of 22° C. after addition of 100 mM of IPTG and subjected to inducible expression for 20 h at 180 rpm.

The components of the M9 culture medium are shown in Table 3:

TABLE 3

Components of M9 culture medium

| Components of M9 Culture Medium | Consumption for 1 L | Remark |
|---|---|---|
| 5 × M9 salt | 200 mL | Combined sterilization is allowed (121° C., 20 min) |
| Glycerinum | 4 mL | |
| 0.1M MgSO$_4$ (0.6 g, constant volume of 50 mL) | 20 mL | Separate sterilization (121° C., 20 min) |
| 0.02M CaCl$_2$ (0.11 g, constant volume of 50 mL) | 5 mL | Separate sterilization (121° C., 20 min) |

Components of 5×M9 salt are: 8.55 g/100 mL of Na$_2$HPO$_4$.12H$_2$O, 1.5 g/100 mL of KH$_2$PO$_4$, 0.25 g/100 mL of NaCl and 0.5 g/100 mL of NH$_4$Cl.

3. Determination of Enzyme Activity by Resting Cells Transformation of RA

The OD600 of the bacteria solution was determined. Bacteria were collected by centrifugation (4° C., 10000 g, 2 min). The bacterial pellet was resuspended with 5× volume buffer solution for resting transformation of RA (pH 8.0 sodium phosphate buffer solution, with RA, sucrose and trisodium citrate added). The cell suspension was incubated at 39° C. for 24 h and centrifuged (4° C., 10000 g, 2 min) to collect the cells. The supernatant was lysed with 0.22 m membrane to eliminate impurities such as bacteria debris to obtain a mixture of RD and RM; the concentration of RA, RD and RM in the mixture is determined by HPLC, and the RA transformation rate and RD to RM ratio were calculated. Detailed calculation methods are:

Molar transformation rate of RA=(molar concentration of RD+molar concentration of RM)/(molar concentration of RA+molar concentration of RD+molar concentration of RM)×100%;

Mass transformation rate of RA=(mass concentration of RD+mass concentration of RM)/(mass concentration of RA+mass concentration of RD+mass concentration of RM)×100%; and D/M ratio=molar concentration of RD/molar concentration of RM.

The concentration of substrate RA was 5 g/L, that of sucrose is 40% (w/v) and that of trisodium citrate was 60 mM.

Culture and transformation of the two strains are shown in Table 4:

TABLE 4

| | Strain 1 | Strain 2 |
|---|---|---|
| Chassis | BL21 (DE3) | BL21(DE3)ΔglgCΔpgmΔagpΔushA::operon T5 |
| OD600 of the bacteria solution | 6.51 | 6.63 |
| Mass transformation rate in 24 h | 65.27% | 99.13% |
| D/M molar ratio | 1.73 | 0.01 |

Example 2: Steviol Glycoside Production Using Recombinant *Pichia pastoris*

Primers were designed according to the gene sequence of EUGT11 and UGT76G1, the restriction enzyme cutting sites, EcoRI and KpnI, were introduced. A terminator sequence was introduced at the downstream of EUGT11. Sequences of the primer are:

F:
(SEQ ID NO: 23)
5'-CCGGAATTCAAAACAAAACCGAAACCACCGTT-3'

R:
(SEQ ID NO: 24)
5'-CGGGGTACCTCATTAACTAGTCAGAGAAGAGATGTA-3'

Sequences of the primer for UGT76G1 are:

F:
(SEQ ID NO: 25)
5'-CCGGAATTCAAAACAAAACCGAAACCACCGTT-3'

R:
(SEQ ID NO: 26)
5'-CGGGGTACCTTAACTAGTCAGAGAAGAGATGTA-3'

The gene segments were obtained through PCR, and subject to double digestion along with the pPICZA carrier using EcoRI and KpnI. The gene segments (insert) was ligated to obtain recombinant plasmids pPICZA-EUGT11 and pPICZA-UGT76G1.

Primers were designed according to the sequence of AOX1 promoter on pPICZA and the sequences ended with 3' of UGT76G1. Sequences of the primer are:

F:
(SEQ ID NO: 27)
5'-CCGCTCGAGTCATCATTATTAGCTTACTTTCATAATTGCGA-3'

R:
(SEQ ID NO: 28)
5'-ATTTGCGGCCGCTTAACTAGTCAGAGAAGAGATGTA-3'

The pPICZA-UGT76G1 is taken as the template and complete expression sequence is obtained through PCR. Double digestion is carried out to the PCR product segment and pPICZA-EUGT11 recombinant plasmid respectively with XhoI and NotI and then connected to obtain the co-expression plasmid pPICZA-EUGT11-UGT76G1. The unmodified *Pichia pastoris* GS115 and GS115ΔglgCΔpgmΔagpΔushΔ competent cells were transformed through electrical shock. Positive clones were selected through resistance screening and expression strain 3 and strain 4 of recombinant yeast were obtained for fermentation and transformation of RA.

Strain Culture and Expression

Recombinant yeast were selected and inoculated to a 20 ml YPG culture medium (yeast extract powder 1%, peptone 2%, glycerinum 2% and bleomycin 100 mg/L), and cultured for 24 h at 30° C. and 150 rpm. Then, 1% of the obtained yeast was inoculated to a BMMY culture medium (yeast extract powder 1%, peptone 2%, YNB 1.34%, biotin $4 \times 10^{-5}$%, phosphate 100 mM, methanol 0.5%, pH 6.0) and cultured at 30° C. and 150 rpm. 0.5% methanol is added every 24 h. The obtained yeast was cultured for 72 h and then bottled.

Determination of Enzyme Activity by Resting Cells Transformation of RA

OD600 of the yeast cell solution was determined and the cells were centrifuged (4° C., 10000 g, 2 min) was carried out to collect the cells. The cells were resuspended with 5× volume buffer solution for resting transformation at 37° C. for 24 h (pH 8.0 sodium phosphate buffer solution, with substrate, sucrose and trisodium citrate added), and centrifuged at room temperature and 12000 rpm for 2 min. The supernatant was filtrated with 0.22 m membrane to eliminate impurities such as cell debris, thus a mixture of RD and RM was obtained. The concentration of RA, RD and RM in the mixture was determined by HPLC, and the RA transformation rate and RD to RM ratio were calculated. Wherein, the concentration of substrate RA is 5 g/L, that of sucrose is 40% (w/v) and that of trisodium citrate is 60 mM.

Culture and transformation of the two strains are shown in Table 5:

TABLE 5

Culture and transformation of yeast strains

|  | Strain 3 | Strain 4 |
|---|---|---|
| Chassis | GS115 | GS115ΔglgCΔpgmΔagpΔushA |
| OD600 of the yeast solution | 16.5 | 15.9 |
| Mass transformation rate in 24 h | 43.9 | 85.14 |
| D/M ratio | 3.13 | 0.15 |

Example 3: Biotransformation of Substrate RA Using *E. coli*

Biotransformation was carried out by using the strain 2 constructed in Example 1 as the catalyst. A proper amount of substrate RA, sucrose, trisodium citrate and phosphate buffer solution is weighed, dissolved and, after addition of bacteria, mixed until uniformity. The product was obtained through resting reaction. Some parameters during transformation are changed as shown in Table 6 and the transformation rate was determined based on sampling at regular intervals.

TABLE 6

Catalysis System of Recombinant *Escherichia coli*

| Reaction Parameter | Group 1 | Group 2 | Group 3 | Group 4 |
|---|---|---|---|---|
| OD600 | 100 | 80 | 120 | 110 |
| Concentration of RA (g/L) | 5 | 1 | 10 | 80 |
| $Na_2HPO_4/NaH_2PO_4$ | | 100 mmol/L | | |
| Concentration of Trisodium Citrate (mM) | 60 | 50 | 70 | 80 |
| Concentration of Sucrose (%, w/v) | 30 | 40 | 50 | 60 |
| pH | 7.0 | 7.2 | 7.5 | 8.0 |
| Reaction Temperature (° C.) | 36 | 37 | 38 | 40 |
| Reaction Time (h) | 200 | 160 | 140 | 120 |
| Transformation Rate (%) | 99.3 | 99.1 | 92.4 | 48.7 |
| D/M Molar Concentration Ratio | 0.77:100 | 0.04:100 | 2.23:100 | 211:100 |

Example 4: Extraction of RD and RM in the Transformation Solution

Preliminary Separation of the Transformation Solution

The mixed solution after transformation of *Escherichia coli* or saccharomycetes was diluted with purified water to 1.5 times the original volume, 0.5% (w/v) filter aid (e.g., diatomaceous earth) was added, and clear solution was obtained through frame filtration.

Separation by Ultrafiltration Membrane

The clear solution is filtered with 10 kD ultrafiltration membrane, transmembrane pressures are respectively controlled at 0.5 MPa, 1.0 MPa and 1.5 MPa, retentate and ultrafiltrate were taken to detect the solid contents and investigate the influence of transmembrane pressure in ultrafiltration on rebaudioside D/M ultrafiltrate quantity.

When the transmembrane pressure was ≥1.0 MPa, rebaudioside D/M passed through the 10 kD ultrafiltration membrane, achieving separation of product from macromolecular impurities.

TABLE 7

Influence of Transmembrane Pressure in Ultrafiltration on Recovery of α-Glucosyltransferase

| Sampling Position | Pressure (MPa) | | | | | |
|---|---|---|---|---|---|---|
| | 0.5 | | 1.0 | | 1.5 | |
| | Retentate | Ultrafiltrate | Retentate | Ultrafiltrate | Retentate | Ultrafiltrate |
| Content (g/100 mL) | 2.412 | 0 | 1.506 | 1.083 | 1.022 | 1.332 |

Separation Gathering Through Ultrafiltration Membrane

The clear solution was filtered with 10 kD ultrafiltration membrane, and the transmembrane pressure was controlled at 1.5 MPa. The ultrafiltration permeate was filtered with 0.5 kD nanofiltration membrane, and the transmembrane pressures are respectively controlled at 1.0 MPa, 1.5 MPa and 2.0 MPa. The retentate and ultrafiltrate are taken to detect the solid contents and investigate the influence of transmembrane pressure in nanofiltration on elimination of remaining sucrose and micromolecular impurities.

TABLE 8

Influence of Transmembrane Pressure in Nanofiltration on Elimination of Remaining Sucrose and Micromolecular Impurities

| Sampling Position | Pressure (MPa) | | | | | |
|---|---|---|---|---|---|---|
| | 1.0 | | 1.5 | | 2.0 | |
| | Retentate | Ultrafiltrate | Retentate | Ultrafiltrate | Retentate | Ultrafiltrate |
| Content (g/100 mL) | 1.408 | 0 | 1.154 | 0.183 | 1.076 | 0.332 |

When the transmembrane pressure was ≥1.5 MPa, the remaining maltose and micromolecular impurities passed through the 0.5 kD nanofiltration membrane, achieving separation of remaining sucrose and micromolecular impurities from rebaudioside D/M.

Crystallization

The retentate was heated and concentrated to a solid content of 20%, mixed at room temperature for 14 h to precipitate RM crystal, filtered and washed with a small amount of purified water, and then dried to obtain crude RD. The crystallized mother solution was re-concentrated to 1/10 of the original volume and mixed at 4° C. for 14 h to crystallize. The crystal is collected and washed with a small amount of purified water, and then dried to obtain crude RD.

Refinement

50% ethanol solution 10 times the volume of the crude RD or RM was added hereto. The obtained solution is heated and dissolved to generate oversaturated solution, which was mixed for 30 min while it was hot after addition of 1% active carbon, filtered, mixed at 4° C. for 14 h, and then crystallized. The crystal is filtered, collected and dried at 80° C. to obtain rebaudioside D or rebaudioside M with purity >95%.

Example 5: Evaluation of Sweetener Compositions

A sweetener composition I of the invention consists of rebaudioside D and rebaudioside M at a ratio of rebaudioside D:rebaudioside M of 1.5-9:1 by weight. Studies show that RD and RM can supplement each other after being mixed in a certain proportion, thus improving the taste of the sweetener, and allowing the sweetener to be similar to sucrose in taste. In addition, RD and RM, after being mixed, can improve water solubility.

Sensory Analysis

The sweetener composition shall be tested, evaluated and analyzed by referring to *Sensory Analysis Methodology* (*Triangular Test*) (BS ISO 4120) and *Sensory Analysis Method* (*Triangle Test*) (GB/T 12311). The specific analysis method is as follows:

Method and principle: A group of three samples shall be provided to evaluators, two of which are identical and the evaluators shall select a single sample.

Equipment: The test leader shall select equipment according to the nature of products and the number of samples. The equipment used shall not affect test results. Standard equipment that meets test needs shall be preferred.

Sampling: Sampling shall be carried out according to the sampling standard of the product under test. If there is no such standard or the sampling standard is not fully applicable, the sampling method shall be agreed upon by all parties concerned through consultation.

Environment: The requirements of *Sensory Analysis-Methodology-General guidance* (GB/T 10220) shall be met.

Qualifications of evaluators are the conditions specified in GB/T 10220 shall be met, and all evaluators shall have the same qualification and test capability.

Number of evaluators: The number of evaluators shall be determined according to test purposes and significance levels, generally more than 6 experts, or more than 15 preferred evaluators, or more than 25 primary evaluators. More than 7 experts are required at a significance level of 0.1%.

Test leader: The test leader shall not participate in test in general, and shall not know the sample number in case of presence. The test leader may give a brief introduction on relevant issues and the nature of samples without affecting the evaluation. When contaminants have to be tested, a non-contaminant sample and a control contaminant sample shall be provided.

Preparation of test samples: Enough samples A and B shall be provided, and every three test samples are a group.

Sample groups with equal number of samples shall be prepared from laboratory samples in the following six combinations: ABB, AAB, ABA, BAA, BBA and BAB.

Test requirements: Evaluators shall not make conclusion as to the nature of samples from sample supply methods. All test sample groups shall be prepared in the same way [the same equipment, the same container, the same quantity of products and the same arrangement (triangle, straight line, etc.)]. In any sample group, the temperature of test samples shall be the same, and if possible, the temperature of all other sample groups in the test series provided shall also be the same. Test sample containers shall be numbered generally with three random digits. The number shall be different for each test.

Test techniques: Evaluators shall be notified of the test purpose to the extent that their conclusions are not biased. Groups of prepared samples shall be randomly assigned to the evaluators, then the evaluators shall check test samples of each group in the specified order, and the order shall be the same in the same series of tests. While evaluating three test samples in the same group, the evaluators shall have the opportunity to retest each sample. The test leader can tell the evaluators the quantity and volume of samples provided when necessary. When the number of evaluators is less than a multiple of 6, the following two approaches can be taken. (a) Discard redundant sample groups, or (b) Provide each evaluator with six groups of samples for retest.

When the evaluator cannot identify the difference, the answer "no difference" is allowed.

Expression of Results:

The number of "difference" or "no difference" answers shall be counted. When the number of evaluators (n) is greater than 100, the minimum number of answers needed to determine the significant difference in the triangle test at different significance levels (X) is calculated according to the following formula, and the nearest integer value shall be taken. Where, α is the significance level, which is an expected value.

$$X = 0.4714Z\sqrt{n} + \frac{(2n+3)}{6}$$

Where, the value of Z varies according to the significance level α:

α≤0.05 Z=1.64
α≤0.01 Z=2.33
α≤0.001 Z=3.10

In statistical hypothesis test, the probability value of a recognized small probability event is referred to as the significance level of the statistical hypothesis test, and is denoted as α. The smaller the value of α is, the higher the significance level of the hypothesis test is. For example, α is set to 0.05, which means that 95% of samples in the sampling distribution are counted as normal samples and 5% of the samples at both ends are counted as extreme samples. If a sample is classified into 95% of normal samples, it can be considered to be from this population, or the difference between the sample and other samples in this population is just an accidental sampling error, and there is no statistically significant difference. If a sample is classified into 5% of extreme samples, it can be asserted that the sample comes from another population other than this population, or the difference between the sample and other samples in this population is not a sampling error, and there is statistically significant difference.

In the example, "a significance level of 0.1% (α≤0.001) indicates that there is difference", which corresponds to "dissimilar"; "a significance level of 5% (α≤0.05) indicates that there is no difference", which corresponds to "similar"; "a significance level of 1% (α≤0.01) indicates that there is no difference", which corresponds to "very similar"; and "a significance level of 0.1% (α≤0.001) indicates that there is no difference", which corresponds to "no difference".

When the answer "no difference" accounts for a large proportion, it indicates that the difference between two samples is lower than the threshold perceived by evaluators.

Evaluation I

The above evaluation and analysis methods were applied to analyze different compositions, with sucrose as the control sample. Samples and the control sample were prepared respectively into aqueous solutions with the same sweetness and then tested according to the requirements of the above-mentioned sensory analysis method. Effective evaluators are 135 primary evaluators, who were allowed to answer "no difference". The results of taste comparison test are shown in Table 9.

TABLE 9

Taste comparison evaluation

| Sample | Control sample | Number of evaluators | Difference | No difference | Significance level | Conclusion |
| --- | --- | --- | --- | --- | --- | --- |
| RD | Sucrose | 135 | 79 | 56 | A significance level of 5% (α ≤ 0.05) indicates that there is no difference. | Similar |
| RM | Sucrose | 135 | 97 | 38 | A significance level of 0.1% (α ≤ 0.001) indicates that there is difference. | Dissimilar |
| DM 1:9 mixture | Sucrose | 135 | 95 | 40 | A significance level of 0.1% (α ≤ 0.001) indicates that there is difference. | Dissimilar |
| DM 1:4 mixture | Sucrose | 135 | 92 | 43 | A significance level of 0.1% (α ≤ 0.001) indicates that there is difference. | Dissimilar |
| DM 1:1 mixture | Sucrose | 135 | 90 | 45 | A significance level of 0.1% (α ≤ 0.001) indicates that there is difference. | Dissimilar |
| DM 1.5:1 mixture | Sucrose | 135 | 81 | 54 | A significance level of 5% (α ≤ 0.05) indicates that there is no difference. | Similar |

TABLE 9-continued

Taste comparison evaluation

| Sample | Control sample | Number of evaluators | Difference | No difference | Significance level | Conclusion |
|---|---|---|---|---|---|---|
| DM 3:1 mixture | Sucrose | 135 | 78 | 57 | A significance level of 5% ($\alpha \leq 0.05$) indicates that there is no difference. | Similar |
| DM 4:1 mixture | Sucrose | 135 | 77 | 58 | A significance level of 5% ($\alpha \leq 0.05$) indicates that there is no difference. | Similar |
| DM 9:1 mixture | Sucrose | 135 | 75 | 60 | A significance level of 1% ($\alpha \leq 0.01$) indicates that there is no difference. | Very similar |

In Table 9, the DM 1:9 mixture, the DM 1:1 mixture and the DM 1:4 mixture were obtained by mixing RD (>95%) and RM (>95%). The DM 3:1 mixture, the DM 1.5:1 mixture, the DM 4:1 mixture and the DM 9:1 mixture were prepared as described in examples 1 to 4 of the invention. The data in Table 9 shows that the product obtained by the production method of the invention is similar to sucrose in taste. And when the ratio of high purity rebaudioside D (>95%) to high purity rebaudioside M (>95%) (w/w) is 1.5-9:1, the product is similar to sucrose in taste.

Evaluation II

A mixture of rebaudioside D and rebaudioside M at a ratio of 3:1 by weight (DM 3:1 mixture) was mixed with rebaudioside A (RA) at a certain ratio by weight to obtain a sweetener composition.

Rebaudioside A (>97%), DM 3:1 mixture, DM 3:1 mixture-rebaudioside A (1:9, w/w), DM 3:1 mixture-rebaudioside A (9:1, w/w), DM 3:1 mixture-rebaudioside A (3:7, w/w) were analyzed according to the evaluation and analysis methods described above, with sucrose as the control sample. Samples and the control sample were prepared respectively into aqueous solutions with the same sweetness and then tested according to the requirements of the above-mentioned sensory analysis method. Effective evaluators are 135 primary evaluators, who were allowed to answer "no difference". The results of taste comparison test were shown in Table 10.

TABLE 10

Evaluation of comparison test

| Sample | Control sample | Number of evaluators | Difference | No difference | Significance level | Conclusion |
|---|---|---|---|---|---|---|
| Rebaudioside A | Sucrose | 135 | 85 | 50 | A significance level of 0.1% ($\alpha \leq 0.001$) indicates that there is difference. | Dissimilar |
| DM3:1 mixture | Sucrose | 135 | 76 | 59 | A significance level of 5% ($\alpha \leq 0.05$) indicates that there is no difference. | Similar |
| DM3:1 mixture-rebaudioside A (1:9, w/w) | Sucrose | 135 | 79 | 56 | A significance level of 5% ($\alpha \leq 0.05$) indicates that there is no difference. | Similar |
| DM3:1 mixture-rebaudioside A (9:1, w/w) | Sucrose | 135 | 78 | 57 | A significance level of 5% ($\alpha \leq 0.05$) indicates that there is no difference. | Similar |

TABLE 10-continued

Evaluation of comparison test

| Sample | Control sample | Number of evaluators | Difference | No difference | Significance level | Conclusion |
|---|---|---|---|---|---|---|
| DM3:1 mixture-rebaudioside A (3:7, w/w) | Sucrose | 135 | 75 | 60 | A significance level of 1% ($\alpha \leq 0.01$) indicates that there is no difference. | Very similar |

According to the above data, when the ratio of the mixture of rebaudioside D-rebaudioside M (3:1, w/w) to high purity rebaudioside A (>97%) (w/w) is 1:9-9:1, the sweetener composition was similar to sucrose in taste.

Evaluation III

A mixture of rebaudioside D and rebaudioside M at a ratio of 3:1 by weight (DM 3:1 mixture) was mixed with rebaudioside A (RA) at a certain ratio by weight to obtain a sweetener composition.

Rebaudioside A (>97%), DM 3:1 mixture, DM 3:1 mixture-rebaudioside A (3:7, w/w), DM 3:1 mixture-rebaudioside A (7:3, w/w), DM 3:1 mixture-rebaudioside A (4:6, w/w) were analyzed according to the evaluation and analysis methods described above, with sucrose as the control sample. Samples and the control sample were prepared respectively into aqueous solutions with the same sweetness and then tested according to the requirements of the above-mentioned sensory analysis method. Effective evaluators are 125 primary evaluators, who were allowed to answer "no difference". The results of taste comparison test were shown in Table 11.

According to the above data, when the ratio of the mixture of rebaudioside D-rebaudioside M (3:1, w/w) to high purity rebaudioside A (>97%) (w/w) is 3:7-7:3, the sweetener composition is very similar to sucrose in taste.

Evaluation IV

A mixture of rebaudioside D and rebaudioside M at a ratio of 3:1 by weight (DM 3:1 mixture) was mixed with rebaudioside A (RA) at a certain ratio by weight to obtain a sweetener composition.

Rebaudioside A (>97%), DM 3:1 mixture, DM 3:1 mixture-rebaudioside A (4:6, w/w), DM 3:1 mixture-rebaudioside A (6:4, w/w), DM 3:1 mixture-rebaudioside A (5:5, w/w) were analyzed according to the evaluation and analysis methods described above, with sucrose as the control sample. Samples and the control sample were prepared respectively into aqueous solutions with the same sweetness and then tested according to the requirements of the above-mentioned sensory analysis method. Effective evaluators are 128 primary evaluators, who were allowed to answer "no difference". The results of taste comparison test were shown in Table 12.

TABLE 11

| Sample | Control sample | Number of evaluators | Difference | No difference | Significance level | Conclusion |
|---|---|---|---|---|---|---|
| Rebaudioside A | Sucrose | 125 | 78 | 47 | A significance level of 0.1% ($\alpha \leq 0.001$) indicates that there is difference. | Dissimilar |
| DM 3:1 mixture | Sucrose | 125 | 73 | 52 | A significance level of 5% ($\alpha \leq 0.05$) indicates that there is no difference. | Similar |
| DM3:1 mixture-rebaudioside A (3:7, w/w) | Sucrose | 125 | 68 | 57 | A significance level of 1% ($\alpha \leq 0.01$) indicates that there is no difference. | Very similar |
| DM3:1 mixture-rebaudioside A (7:3, w/w) | Sucrose | 125 | 69 | 56 | A significance level of 1% ($\alpha \leq 0.01$) indicates that there is no difference. | Very similar |
| DM3:1 mixture-rebaudioside A (4:6, w/w) | Sucrose | 125 | 58 | 67 | A significance level of 0.1% ($\alpha \leq 0.001$) indicates that there is no difference. | No difference |

TABLE 12

| Sample | Control sample | Number of evaluators | Difference | No difference | Significance level | Conclusion |
|---|---|---|---|---|---|---|
| Rebaudioside A | Sucrose | 128 | 82 | 46 | A significance level of 0.1% ($\alpha \leq 0.001$) indicates that there is difference. | Dissimilar |
| DM 3:1 mixture | Sucrose | 28 | 75 | 53 | A significance level of 5% ($\alpha \leq 0.05$) indicates that there is no difference. | Similar |
| DM3:1 mixture-rebaudioside A (4:6, w/w) | Sucrose | 128 | 59 | 69 | A significance level of 0.1% ($\alpha \leq 0.001$) indicates that there is no difference. | No difference |
| DM3:1 mixture-rebaudioside A (6:4, w/w) | Sucrose | 128 | 58 | 70 | A significance level of 0.1% ($\alpha \leq 0.001$) indicates that there is no difference. | No difference |
| DM3:1 mixture-rebaudioside A (5:5, w/w) | Sucrose | 128 | 50 | 78 | A significance level of 0.1% ($\alpha \leq 0.001$) indicates that there is no difference. | No difference |

According to the above data, when the ratio of the mixture of rebaudioside D-rebaudioside M (3:1, w/w) to high purity rebaudioside A (>97%) (w/w) is 4:6-6:4, the sweetener composition has no difference in taste with sucrose.

Sequences and Seq Id Numbers

The instant disclosure comprises a number of nucleic acid and polypeptide sequences. For convenience, Table 13 correlates each sequence with its appropriate description and SEQ ID NO.

TABLE 13

Description of Sequences and SEQ ID Nos

| SEQ ID NO: | SEQUENCE | DESCRIPTION |
|---|---|---|
| 1 | GGCCCGCTCGGCCGCTCCACGCGCGCACCGGCCCCCTTCTTCCGTCATGGACTCCGGCTACTCCTCCTCC TACGCCGCCGCCGCCGGGATGCACGTCGTGATCTGCCCGTGGCTCGCCTTCGGCCACCTGCTCCCGTGCC TCGACCTCGCCCAGCGCCTCGCGTCGCGGGCCACCGCGTGTCGTTCGTCTCCACGCCGCGGAACATATC CCGCCTCCCGCCGGTGCGCCCCGCGCTCGCGCCGCTCGTCGCCTTCGTGGCGCTGCCGCTCCCGCGCGTC GAGGGGCTCCCCGACGGCGCCGAGTCCACCAACGACGTCCCCCACGACAGGCCGGACATGGTCGAGCTCC ACCGGAGGGCCTTCGACGGGCTCGCCGCGCCCTTCTCGGAGTTCTTGGGCACCGCGTGCGCCGACTGGGT CATCGTCGACGTCTTCCACCACTGGGCCGCAGCCGCCGCTCTCGAGCACAAGGTGCCATGTGCAATGATG TTGTTGGGCTCTGCACATATGATCGCTTCCATAGCAGACAGACGGCTCGAGCGCGCGGAGACAGAGTCGC CTGCGGCTGCCGGGCAGGGACGCCCAGCGGCGGCGCCAACGTTCGAGGTGGCGAGGATGAAGTTGATACG AACCAAAGGCTCATCGGGAATGTCCCTCGCCGAGCGCTTCTCCTTGACGCTCTCGAGGAGCAGCCTCGTC GTCGGGCGGAGCTGCGTGGAGTTCGAGCCGGAGACCGTCCCGCTCCTGTCGACGCTCCGCGGTAAGCCTA TTACCTTCCTTGGCCTTATGCCGCCGTTGCATGAAGGCCGCCGCGAGGACGGCGAGGATGCCACCGTCCG CTGGCTCGACGCGCAGCCGGCCAAGTCCGTCGTGTACGTCGCGCTAGGCAGCGAGGTGCCACTGGGAGTG GAGAAGGTCCACGAGCTCGCGCTCGGGCTGGAGCTCGCCGGAGCGCACGCGCGGCCGCGGCGTCGT GGCGACGAGATGGGTTCCTCAGATGAGCATACTGGCGCACGCGCCGTGGGCGCGTTCCTGACCCACTGC GGCTGGAACTCGACCATCGAGGGGCTCATGTTCGGCCACCCGCTTATCATGCTGCCGATCTTCGGCGACC AGGGACCGAACGCGCGGCTAATCGAGGCGAAGAACGCCGGATTGCAGGTGGCAAGAAACGACGGCGATGG ATCGTTCGACCGAGAAGGCGTCGCGGCGGCGATTCGTGCAGTCGCGGTGGAGGAAGAAAGCAGCAAAGTG TTTCAAGCCAAAGCCAAGAAGCTGCAGGAGATCGTCGCGGACATGGCCTGCCATGAGAGGTACATCGACG | EUGT11 gene NCBI No. AK121682.1 |

TABLE 13-continued

Description of Sequences and SEQ ID Nos

| SEQ ID NO: | SEQUENCE | DESCRIPTION |
|---|---|---|
| | GATTCATTCAGCAATTGAGATCTTACAAGGATTGAAGCATCTCAGGATGTACACCTGCAACAGTGCAACT ACAAAATCCTTGGAATAAAATGATTTTGTTTTGTAGTCC | |
| 2 | ARSAAPRAHRPPSSVMDSGYSSSYAAAAGMHVVICPWLAFGHLLPCLDLAQRLASRGHRVSFVSTPRNISR LPPVRPALAPLVAFVALPLPRVEGLPDGAESTNDVPHDRPDMVELHRRAFDGLAAPFSEFLGTACADWVIV DVFHHWAAAAALEHKVPCAMMLLGSAHMIASIADRRLERAETESPAAAGQGRPAAAPTFEVARMKLIRTKG SSGMSLAERFSLTLSRSSLVVGRSCVEFEPETVPLLSTLRGKPITFLGLMPPLHEGRREDGEDATVRWLDA QPAKSVVYVALGSEVPLGVEKVHELALGLELAGTRFLWALRKPTGVSDADLLPAGFEERTRGRGVVATRWV PQMSILAHAAVGAFLTHCGWNSTIEGLMFGHPLIMLPIFGDQGPNARLIEAKNAGLQVARNDGDGSFDREG VAAAIRAVAVEEESSKVFQAKAKKLQEIVADMACHERYIDGFIQQLRSYKD-SISGCTPATVQLQNPWNKM IFVL-S | Translation of EUGT11 gene (NCBI No. AK121682.1) |
| 3 | ARSAAPRAHRPPSSVMDSGYSSSYAAAAGMHVVICPWLAFGHLLPCLDLAQRLASRGHRVSFVSTPRNISR LPPVRPALAPLVAFVALPLPRVEGLPDGAESTNDVPHDRPDMVELHRRAFDGLAAPFSEFLGTACADWVIV DVFHHWAAAAALEHKVPCAMMLLGSAHMIASIADRRLERAETESPAAAGQGRPAAAPTFEVARMKLIRTKG SSGMSLAERFSLTLSRSSLVVGRSCVEFEPETVPLLSTLRGKPITFLGLMPPLHEGRREDGEDATVRWLDA QPAKSVVYVALGSEVPLGVEKVHELALGLELAGTRFLWALRKPTGVSDADLLPAGFEERTRGRGVVATRWV PQMSILAHAAVGAFLTHCGWNSTIEGLMFGHPLIMLPIFGDQGPNARLIEAKNAGLQVARNDGDGSFDREG VAAAIRAVAVEEESSKVFQAKAKKLQEIVADMACHERYIDGFIQQLRSYKD- | Translation of EUGT11 gene (NCBI No. AK121682.1) |
| 4 | CTTGCGTGTAAACGTCAGTCAAACCCAATGGAAAATAAAACGGAGACCACCGTTCGCCGGCGCCGGAGAA TAATATTATTCCCGGTACCATTTCAAGGCCACATTAACCCAATTCTTCAGCTAGCCAATGTGTTGTACTC TAAAGGATTCAGTATCACCATCTTTCACACCAACTTCAACAAACCCAAAACATCTAATTACCCTCACTTC ACTTTCAGATTCATCCTCGACAACGACCCACAAGACGAACGCATTTCCAATCTACCGACTCATGGTCCGC TCGCTGGTATGCGGATTCCGATTATCAACGAACACGGAGCTGACGAATTACGACGCGAACTGGAACTGTT GATGTTAGCTTCTGAAGAAGATGAAGAGGTATCGTGTTTAATCACGGATGCTCTTTGGTACTTCGCGCAA TCTGTTGCTGACAGTCTTAACCTCCGACGGCTTGATTTTGATGACAAGCAGCTTGTTTAATTTTCATGCAC ATGTTTCACTTCCTCAGTTTGATGAGCTTGGTTACCTCGATCCTGATGACAAAACCCGTTTGGAAGAACA AGCGAGTGGGTTTCCTATGCTAAAAGTGAAAGACATCAAGTCTGCGTATTCGAACTGGCAAATACTCAAA GAGATATTAGGGAAGATGATAAAACAAACAAAAGCATCTTCAGGAGTCATCTGGAACTCATTTAAGGAAC TCGAAGAGTCTGAGCTCGAAACTGTTATCCGTGAGATCCCGGCTCCAAGTTTCTTGATACCACTCCCCAA GCATTTGACAGCCTCTTCCAGCAGCTTACTAGACCACGATGTCGAACCGTTTTTCAATGGTTAGACCAACAA CCGCCAAGTTCGGTACTGTATGTTAGTTTTGGTAGTACTAGTGAAGTGGATGAGAAAGATTTCTTGGAAA TAGCTCGTGGGTTGGTTGATAGCAAGCAGTCGTTTTTATGGGTGGTTCGACCTGGGTTTGTCAAGGGTTC GACGTGGGTCGAACCGTTGCCAGATGGTTCTTGGGTGAAAGAGGACGTATTGTGAAATGGGTTCCACAG CAAGAAGTGCTAGCTCATGGAGCAATAGGCGCATTCTGGACTCACAGCGGATGGAACTCTACGTTGGAAA GCGTTTGTGAAGGTGTTCCTATGATTTTCTCGGATTTTGGGCTCGATCAACCGTTGAATGCTAGATACAT GAGTGATGTTTTGAAGGTAGGGGTGTATTTGGAAAATGGGTGGGAAAGAGGAGAGATAGCAAATGCAATA AGAAGAGTTATGGTGGATGAAGAAGGAGAATACATTAGACAGAATGCAAGAGTTTTGAAACAAAAGGCAG ATGTTTCTTTGATGAAGGGTGGTTCGTCTTACTCAGAATCATTGAGTGTCTCTAGTTTCTTACATTTCATCGTT GTAAATAACACGATGATTAATCAAGCACTTGGATTGCATGCTAGCTGAGTAGCTGGTAATTTGAGTTATT AGAAGCAAAGACTACTTGGTTTAAATTAAATAAAGGATGGTTGTTGGTTATGTGAGCTAGTTTATGTTAT GTTTTGTAGGCTATAAAAGCCTTCATATGTTTCTTATTGTTTCTGTTTCTAAGGTGAAAAAAATGCTCGT TTTTAT | UGT76G1 gene NCBI No. AY345974.1 |
| 5 | LACKRQSNPMENKTETTVRRRRIILFPVPFQGHINPILQLANVLYSKGFSITIFHTNFNKPKTSNYPHFT FRFILDNDPQDERISNLPTHGPLAGMRIPIINEHGADELRRELELLMLASEEDEEVSCLITDALWYFAQSV ADSLNLRRLVLMTSSLFNFHAHVSLPQFDELGYLDPDDKTRLEEQASGFPMLKVKDIKSAYSNWQILKEIL GKMIKQTKASSGVIWNSFKELEESELETVIREIPAPSFLIPLPKHLTASSSSLLDHDRTVFQWLDQQPPSS VLYVSFGSTSEVDEKDFLEIARGLVDSKQSFLWVVRPGFVKGSTWVEPLPDGFLGERGRIVKWVPQQEVLA HGAIGAFWTHSGWNSTLESVCEGVPMIFSDFGLDQPLNARYMSDVLKVGVYLENGWERGEIANAIRRVMVD EEGEYIRQNARVLKQKADVSLMKGGSSYESLESLVSYISSL-ITR-LIKHLDCMLAE-LVI-VIRSKDYLV -IK-RMVVGYVS-FMLCFVGYKSLHMFLIVSVSKVKKMLVF | Translation of UGT76G1 gene (NCBI No. AY345974.1) |
| 6 | MENKTETTVRRRRIILFPVPFQGHINPILQLANVLYSKGFSITIFHTNFNKPKTSNYPHFT FRFILDNDPQDERISNLPTHGPLAGMRIPIINEHGADELRRELELLMLASEEDEEVSCLITDALWYFAQSV ADSLNLRRLVLMTSSLFNFHAHVSLPQFDELGYLDPDDKTRLEEQASGFPMLKVKDIKSAYSNWQILKEIL GKMIKQTKASSGVIWNSFKELEESELETVIREIPAPSFLIPLPKHLTASSSSLLDHDRTVFQWLDQQPPSS VLYVSFGSTSEVDEKDFLEIARGLVDSKQSFLWVVRPGFVKGSTWVEPLPDGFLGERGRIVKWVPQQEVLA HGAIGAFWTHSGWNSTLESVCEGVPMIFSDFGLDQPLNARYMSDVLKVGVYLENGWERGEIANAIRRVMVD EEGEYIRQNARVLKQKADVSLMKGGSSYESLESLVSYISSL | Translation of UGT76G1 gene (NCBI No. AY345974.1) |
| 7 | MENKTETTVRRRRIILFPVPFQGHINPILQLANVLYSKGFSITIFHTNFNKPKTSNYPHFTFRFILDND PQDERISNLPTHGPLAGMRIPIINEHGADELRRELELLMLASEEDEEVSCLITDALWYFAQSVADSLNLR RLVLMTSSLFNFHAHVSLPQFDELGYLDPDDKTRLEEQASGFPMLKVKDIKSAYSNWQILKEILGKMIKQ TKASSGVIWNSFKELEESELETVIREIPAPSFLIPLPKHLTASSSSLLDHDRTVFQWLDQQPPSSVLYVS FGSTSEVDEKDFLEIARGLVDSKQSFLWVVRPGFVKGSTWVEPLPDGFLGERGRIVKWVPQQEVLAHGAI GAFWTHSGWNSTLESVCEGVPMIFSDFGLDQPLNARYMSDVLKVGVYLENGWERGEIANAIRRVMVDEEG EYIRQNARVLKQKADVSLMKGGSSYESLESLVSYISSL | Protein sequence NCBI No. AAR06912.1 (from Chinese application CN 109234340) |
| 8 | GGTTTCTCTA TCACCATCTT CCACACCAAC TTCAACAAAC CGAAACCCTC TAACTACCCG CACTTCACCT TCCGTTTCAT CCTGGACAAC GACCCGCAGG ACGAACGTAT CTCTAACCTG CCGACCCACG GTCCGCTGGC GGGTATGCGT ATCCCGATCA TCAACGAACA CGGTGCGGAC GAACTGCGTC GTGAACTGGA ACTGCTGATG CTGGCGTCTG AAGAAGACGA AGAAGTTTCT | UGT76G1 gene (from Chinese application CN 109234340) |

TABLE 13-continued

Description of Sequences and SEQ ID Nos

| SEQ ID NO: | SEQUENCE | DESCRIPTION |
|---|---|---|
|  | TGCCTGATCA CCGACGCGCT GTGGTACTTC GCGCAGTCTG TTGCGGACTC TCTGAACCTG<br>CGTCGTCTGG TTCTGATGAC CTCTTCTCTG TTCAACTTCC ACGCGCACGT TTCTCTGCCG<br>CAGTTCGACG AACTGGGTTA CCTGGACCCG GACGACAAAA CCCGTCTGGA AGAACAGGCA<br>TCTGGTTTCC CGATGCTGAA AGTTAAAGAC ATCAAATCTG CGTACTCTAA CTGGCAGATC<br>CTGAAAGAAA TCCTGGGTAA AATGATCAAA CAGACCAAAG CGTCTTCTGG TGTTATCTGG<br>AACTCTTTCA AGAACTGGA AGAATCTGAA CTGGAAACCG TTATCCGTGA AATCCCGGCG<br>CCGTCTTTCC TGATCCCGCT GCCGAAACAC CTGACCGCGT CTTCTTCTTC TCTGCTGGAC<br>CACGACCGTA CCGTTTTCCA GTGGCTGGAC CAGCAGCCGC CGTCTTCTGT TCTGTACGTT<br>TCTTTCGGTT CTACCTCTGA AGTTGACGAA AAAGACTTCC TGGAAATCGC GCGTGGTCTG<br>GTTGACTCTA ACAGTCTTT CCTGTGGGTT GTTCGTCCGG GTTTCGTTAA AGGTTCTACC<br>TGGGTTGAAC CGCTGCCGGA CGGTTTCCTG GGTGAACGTG GTCGTATCGT TAAATGGGTT<br>CCGCAGCAGG AAGTTCTGGC GCACGGTGCG ATCGGTGCGT TCTGGACCCA CTCTGGTTGG<br>AACTCTACCC TGGAATCTGT TTGCGAAGGT GTTCCGATGA TCTTCTCTGA CTTCGGTCTG<br>GACCAGCCGC TGAACGCGCG TTACATGTCT GACGTTCTGA AAGTTGGTGT TTACCTGGAA<br>AACGGTTGGG AACGTGGTGA AATCGCGAAC GCGATCCGTC GTGTTATGGT TGACGAAGAA<br>GGTGAATACA TCCGTCAGAA CGCGCGTGTT CTGAAACAGA AAGCGGACGT TTCTCTGATG<br>AAAGGTGGTT CTTCTTACGA ATCTCTGGAA TCTCTGGTTT CTTACATCTC TTCTCTGACT<br>AGTTAA |  |
| 9 | GFSITIFHTNFNKPKTSNYPHFTFRFILDNDPQDERISNLPTHGPLAGMRIPIINEHGADELRRELELLM<br>LASEEDEEVSCLITDALWYFAQSVADSLNLRRLVLMTSSLFNFRAHVSLPQFDELGYLDPDDKTRLEEQA<br>SGFPMLKVKDIKSAYSNWQILKEILGKMIKQTKASSGVIWNSFKELEESELETVIREIPAPSFLIPLPKH<br>LTASSSSLLDHDRTVFQWLDQQPPSSVLYVSFGSTSEVDEKDFLEIARGLVDSKQSFLWVVRPGFVKGST<br>WVEPLPDGFLGERGRIVKWVPQQEVLAHGAIGAFWTHSGWNSTLESVCEGVPMIFSDFGLDQPLNARYMS<br>DVLKVGVYLENGWERGEIANAIRRVMVDEEGEYIRQNARVLKQKADVSLMKGGSSYESLESLVSYISSLT<br>S | Translation of UGT76G1 gene |
| 10 | MRIPIINEHGADELRRELELLM<br>LASEEDEEVSCLITDALWYFAQSVADSLNLRRLVLMTSSLFNFRAHVSLPQFDELGYLDPDDKTRLEEQA<br>SGFPMLKVKDIKSAYSNWQILKEILGKMIKQTKASSGVIWNSFKELEESELETVIREIPAPSFLIPLPKH<br>LTASSSSLLDHDRTVFQWLDQQPPSSVLYVSFGSTSEVDEKDFLEIARGLVDSKQSFLWVVRPGFVKGST<br>WVEPLPDGFLGERGRIVKWVPQQEVLAHGAIGAFWTHSGWNSTLESVCEGVPMIFSDFGLDQPLNARYMS<br>DVLKVGVYLENGWERGEIANAIRRVMVDEEGEYIRQNARVLKQKADVSLMKGGSSYESLESLVSYISSLT<br>S | Translation of UGT76G1 gene |
| 11 | gRNA: gcagccgttcgtggaagggccaatgacttgggtcgtaagcacctgcatttatttccgttc | pgm gene |
| 12 | gRNA: cgatcgtacatatccagctcttgttaccggaagtatgggttgtagatatggtcgcccgcc | glgC gene |
| 13 | gRNA: agaaaccgttggcatctatcgcatatacggtgtccggcggttgttgatacttcgcgctaa | agp gene |
| 14 | gRNA: ctcgcttttccgtcttccccttgtacagaccaatatgggaccaattttttgctgtgtcat | ushA gene |
| 15 | ATGAAAAACAAGGTGCAGCTCATCACTTACGCCGACCGCCTTGGCGACGGCACCATCAAGTCGATGACCG<br>ACATTCTGCGCACCCGCTTCGACGGCGTGTACGACGGCGTTCACATCCTGCCGTTCTTCACCCCGTTCGA<br>CGGCGCCGACGCAGGCTTCGACCCGATCGACCACACCAAGGTCGACGAACGTCTCGGCAGCTGGGACGAC<br>GTCGCCGAACTCTCCAAGACCCACAACATCATGGTCGACGCCATCGTCAACCACATGAGTTGGGAATCCA<br>AGCAGTTCCAGGACGTGCTGGCCAAGGGCGAGGAGTCCGAATACTATCCGATGTTCCTCACCATGAGCTC<br>CGTGTTCCCGAACGGCGCCACCGAAGAGGACCTGGCCGGCATCTACCGTCCGCGTCCGGGCCTGCCGTTC<br>ACCCACTACAAGTTCGCCGGCAAGACCCGCCTCGTGTGGGTCAGCTTCACCCCGCAGCAGGTGGACATCG<br>ACACCGATTCCGACAAGGGTTGGGAATACCTCATGTCGATTTTCGACCAGATGGCCGCCTCTCACGTCAG<br>CTACATCCGCCTCGACGCCGTCGGCTATGGCGCCAAGGAAGCCGGCACCAGCTGCTTCATGACCCCGAAG<br>ACCTTCAAGCTGATCTCCCGTCTGCGTGAGGAAGGCGTCAAGCGCGGCTCTGGAAATCCTCATCGAAGTGC<br>ACTCCTACTACAAGAAGCAGGTCGAAATCGCATCCAAGGTGACCGCGTCTACGACTTCGCCCTGCCTCC<br>GCTGCTGCTGCACGCGCTGAGCACCGGCCACGTCGAGCCCGTCGCCCACTGGACCGACATACGCCCGAAC<br>AACGCCGTCACCGTGCTCGATACGCACGACGGCATCGGCGTGATCGACATCGGCTCCGACCAGCTCGACC<br>GCTCGCTCAAGGGTCTCGTGCCGGATGAGGACGTGGACAACTCGTCAACAACATCCACGCCAACACCCA<br>CGGCGAATCCCAGGCAGCCACTGGCGCCGCCGCATCCAATCTCGACCTCTACCAGGTCAACAGCACCTAC<br>TATTCGGCGCTCGGGTGCAACGACCAGCACTACATCGCCGCCCGCGGTGCAGTTCTTCCTGCCGGGCG<br>TGCCGCAAGTCTACTACGTCGGCGCGCTCGCCGGCAAGAACGACATGGAGCTGCTGCGTAAGACGAATAA<br>CGGCCGCGACATCAATCGCCATTACTACTCCACCGCGGAAATCGACGAACTCAAGCGCTCCGGTCGTC<br>AAGGCCCTGAACGCGCTCGCCAAGTTCCGCAACGAGCTCGACGCGTTCGACGGCACGTTCTCGTACACCA<br>CCGATGACGACACGTCCATCAGCTTCACCTGGCGCGGCGAAACCAGCCAGGCCACGCTGACGTTCGAGCC<br>GAAGCGCGGTCTCGGTGTGGACAACACTACGCCGGTCGCCATGTTGGAATGGGAGGATTCCGCGGGAGAC<br>CACCGTTCGGATGATCTGATCGCCAATCCGCCTGTCGTCGCCCTGA | BasP gene<br>NCBI Gene ID: 4556453 |
| 16 | MKNKVQLITYADRLGDGTIKSMTDILRTRFDGVYDGVHILPFFTPFDGADAGFDPIDHTKVDERLGSWDDV<br>AELSKTHNIMVDAIVNHMSWESKQFQDVLAKGEESEYYPMFLTMSSVFPNGATEEDLAGIYRPRPGLPFTH<br>YKFAGKTRLVWVSFTPQQVDIDTDSDKGWEYLMSIFDQMAASHVSYIRLDAVGYGAKEAGTSCFMTPKTFK<br>LISRLREEGVKRGLEILIEVHSYYKKQVEIASKVDRVYDFALPPLLLHALSTGHVEPVAHWTDIRPNNAVT<br>VLDTHDGIGVIDIGSDQLDRSLKGLVPDEDVDNLVNTIHANTHGESQAATGAAASNLDLYQVNSTYYSALG<br>CNDQHYIAARAVQFFLPGVPQVYYVGALAGKNDMELLRKTNNGRDINRHYYSTAEIDENLKRPVVKALNAL<br>AKFRNELDAFDGTFSYTTDDDTSISFTWRGETSQATLTFEPKRGLGVDNTTPVAMLEWEDSAGDHRSDDLI<br>ANPPVVA- | Translation of BasP gene |

TABLE 13-continued

Description of Sequences and SEQ ID Nos

| SEQ ID NO: | SEQUENCE | DESCRIPTION |
|---|---|---|
| 17 | ATGTTTGCCGAAGATCTGAAACGGACGGAGAAGATGACAGTGGACGACGTGTTCGAGCAGTCGGCGCAGA<br>AGATGCGCGAGCAGGGCATGAGCGAGATCGCCATCTCGCAGTTCAGGCACGCATACCATGTGTGGGCCAG<br>CGAGAAGGAGAGCGCGTGGATCCGCGAGGACGCCGTCGAGCCGCTGCACGGCGTGCGGAGCTTCCATGAC<br>GTGTACAAGACCATCGATCATGACAAGGCAGTGCACGCGTTCGCCAAGACTGCATTCCTCAAGCTCAACG<br>GCGGCCTGGGAACCTCGATGGGCCTGCAATGCGCGAAGTCGCTGCTGCCGGTGCGCCGCCACAAGGCTCG<br>GCAGATGCGCTTCCTCGACATCATCCTCGGTCAGGTGCTCACCGCGCGACGAGGCTGAACGTGCCTCTG<br>CCCGGTCACGTTCATGAACTCGTTCCGCACTTCGGATGACACGATGAAGGCACTGCGACACCAGCGCAAGT<br>TCAAGCAGACCGACATCCCGCTGGAGATCATCCAGCATCAGGAACCGAAGATCGACGCGGCCACCGGGGC<br>GCCGGCGTCTTGGCCGGCCAACCCCGATCTGGAGTGGTGCCCGCCCGGCCACGGCGACCTGTTCTCGACG<br>CTGTGGGAGTCCGGCCTGCTGGACACTCTGCTGGAGCATGGCTTCGAATACCTGTTCATCTCGAACTCCG<br>ACAATTTGGGTGCGCGCCCGTCTCGCACGCTCGCCCAGTATTTCGAGGATACGGGCGCCCCGTTCATGGT<br>CGAGGTCGCCAATCGCACGTACGCGGACCGCAAGGGTGGCCATATCGTGCGCGACACGGCCACCGGCCGA<br>CTGATCCTGCGGGAGATGTCGCAGGTGCATCCTGACGACAAGGACGCGGCCCAGGACATCGCCAAGCACC<br>CGTATTTCAACACGAACAACATCTGGGTGCGCATCGACGTGCTGCGCGTCATGCTCGCCGAGCATGACGG<br>CGTGCTGCCGCTTCCCGTCATCATCAACAACAAGACCGTCGACCCGACCGACCCCCAGTCCCCGGCCGGTG<br>GTCCAGCTGGAGACTGCGATGGGCGCGGCGATCGGCCTGTTCGAAGGCGCGATCTGTGTGCAGGTGGACC<br>GCATGCGGTTCCTGCCAGTGAAGACGACCAACGACCTGTTCATTATGCGTTCCGATCGGTTCCACCTTAC<br>GGACTCGTATGAGATGGAGGACGGCAACTACATTTTCCCGAACGTGCCGTCGCCGCCGCGAACTCGGTCAGCA<br>TCAAGGGAGACTGGACATTCGGACGTGACGTCATCATGTTCGCCGACGCGCGTCTGGAGGATAGAAACGA<br>GCCCAGTTACGTACCCAACGGCGAATACGTCGGACCGATGGGCATCGAGCCCGGTGATTGGGTGTGA | UgpA gene NCBI GeneID: 9889115 |
| 18 | MFAEDLKRTEKMTVDDVFEQSAQKMREQGMSEIAISQFRHAYHVWASEKESAWIREDAVEPLHGVRSFHDV<br>YKTIDHDKAVHAFAKTAFLKLNGGLGTSMGLQCAKSLLPVRRHKARQMRFLDIILGQVLTARTRLNVPLPV<br>TFMNSFRTSDDTMKALRHQRKFKQTDIPLEIIQHQEPKIDAATGAPASWPANPDLEWCPPGHGDLFSTLWE<br>SGLLDTLLEHGFEYLFISNSDNLGARPSRTLAQYFEDTGAPPMVEVANRTYADRKGGHIVRDTATGRLILR<br>EMSQVHPDDKDAAQDIAKHPYFNTNNIWVRIDVLRVMLAEHDGVLPLPVIINNKTVDPTDPQSPAVVQLET<br>AMGAAIGLFEGAICVQVDRMRFLPVKTTNDLFIMRSDRFHLTDSYEMEDGNYIFPNVDLDPRYYKNIEDFN<br>ERFPYNVPSLAAANSVSIKGDWTFGRDVIMFADARLEDRNEPSYVPNGEYVGPMGIEPGDWV- | Translation of UgpA gene NCBI GeneID: 9889115 |
| 19 | F: 5'-CGCGGATCCATGGACTCCGGCTACTCCTCC-3' | recombinant E. coli EUGT11 PCR amplification primer |
| 20 | R: 5'-CCCAAGCTTTCAATCCTTGTAAGATCTCAATTGC-3 | recombinant E. coli EUGT11 PCR amplification primer |
| 21 | F: 5'-CATGCCATGGAAAACAAAACCGAAACCACCGTT-3' | recombinant E. coli UGT76G1 PCR amplification primer |
| 22 | R: 5'-GGACTAGTTTAACTAGTCAGAGAAGAGATGTA-3' | recombinant E. coli UGT76G1 PCR amplification primer |
| 23 | F: 5'-CCGGAATTCAAAACAAAACCGAAACCACCGTT-3' | Pichia pastoris EUGT11 and UGT76G1 primer |
| 24 | R: 5'-CGGGGTACCTCATTAACTAGTCAGAGAAGAGATGTA-3' | Pichia pastoris EUGT11 and UGT76G1 primer |
| 25 | F: 5'-CCGGAATTCAAAACAAAACCGAAACCACCGTT-3' | Pichia pastoris EUGT11 and UGT76G1 primer |
| 26 | R: 5'-GGACTAGTTTAACTAGTCAGAGAAGAGATGTA-3' | Pichia pastoris EUGT11 and UGT76G1 primer |
| 27 | F: 5'-CCGCTCGAGTCATCATTATTAGCTTACTTTCATAATTGCGA-3' | For recombinant pichia pastoris AOX1 promoter on pPICZA and the sequences ended with 3' of UGT76G1. |

TABLE 13-continued

Description of Sequences and SEQ ID Nos

| SEQ ID NO: | SEQUENCE | DESCRIPTION |
|---|---|---|
| 28 | R: 5'-<u>ATTTGCGGCCGC</u>TTAACTAGTCAGAGAAGAGATGTA-3' | For recombinant *pichia pastoris* AOX1 promoter on pPICZA and the sequences ended with 3' of UGT76G1. |

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

What is claimed is:

1. A method for producing rebaudioside D and/or rebaudioside M, comprising:
providing a starting composition comprising at least one of rebaudioside A and stevioside;
incubating the starting composition with a recombinant microorganism in a mixture, wherein the recombinant microorganism expresses a uridine diphosphate (UDP)-glucosyltransferase enzyme derived from *Oryza sativa* (EUGT11) and a UDP-glucosyltransferase enzyme derived from *Stevia rebaudiana* (UGT76G1); and
purifying rebaudioside D and/or rebaudioside M from the mixture,
wherein the recombinant microorganism is recombinant *Escherichia coli* or recombinant *Pichia pastoris*, and:
when the recombinant microorganism is recombinant *Escherichia coli*, phosphoglucomutase gene (pgm), G1P adenylyl transferase gene (glgC) and G1P phosphatase gene (agp) in the recombinant *Escherichia coli* are knocked out, and the uridine diphosphate glucose (UDPG) synthetase gene (ushA) is replaced with T5 operon containing sucrose phosphorylase (Basp) and G1P uridine acyltransferase (ugpA) genes, and
when the recombinant microorganism is recombinant *Pichia pastoris*, pgm gene, glgC gene and agp gene in the recombinant *Pichia pastoris* are knocked out.

2. A method for producing rebaudioside D and/or rebaudioside M, comprising:
providing a starting composition comprising at least one of rebaudioside A and stevioside;
incubating the starting composition with an enzyme preparation produced by a recombinant microorganism in a mixture, wherein the recombinant microorganism expresses an EUGT11 enzyme of *Oryza sativa* and a UGT76G1 enzyme of *Stevia rebaudiana*;
purifying rebaudioside D and/or rebaudioside M from the mixture,
wherein the recombinant microorganism is recombinant *Escherichia coli* or recombinant *Pichia pastoris*, and:
when the recombinant microorganism is recombinant *Escherichia coli*, pgm gene, glgC gene and agp gene in the recombinant *Escherichia coli* are knocked out, and the UDPG synthetase gene ushA are replaced with T5 operon containing Basp and ugpA genes, and
when the recombinant microorganism is recombinant *Pichia pastoris*, pgm gene, glgC gene and agp gene in the recombinant *Pichia pastoris* are knocked out.

3. The method of claim 1, wherein the incubating step is performed in the presence of sucrose and trisodium citrate.

4. The method of claim 2, wherein the incubating step is performed in the presence of sucrose and trisodium citrate.

5. The method of claim 1, wherein the recombinant microorganism is recombinant *Escherichia coli*.

6. The method of claim 2, wherein the recombinant microorganism is recombinant *Escherichia coli*.

7. The method of claim 1, wherein the recombinant microorganism is recombinant *Pichia pastoris*.

8. The method of claim 2, wherein the recombinant microorganism is recombinant *Pichia pastoris*.

9. The method of claim 3, wherein the recombinant microorganism is a whole cell and the mixture in which the starting composition and the recombinant microorganism are incubated is a cell culture medium.

10. The method of claim 4, wherein the recombinant microorganism is a whole cell and the mixture in which the starting composition and the recombinant microorganism are incubated is a cell culture medium.

11. The method of claim 3, wherein the enzyme preparation is a crude enzyme preparation produced by the recombinant microorganism.

12. The method of claim 4, wherein the enzyme preparation is a crude enzyme preparation produced by the recombinant microorganism.

13. The method of claim 11, wherein the crude enzyme preparation contains glucosyltransferase and some secondary metabolites.

14. The method of claim 12, wherein the crude enzyme preparation contains glucosyltransferase and some secondary metabolites.

15. The method of claim 13, wherein the crude enzyme preparation is produced by cell disruption in the presence of at least 40% of sucrose as a hypertonic solution.

16. The method of claim 14, wherein the crude enzyme preparation is produced by cell disruption in the presence of at least 40% of sucrose as a hypertonic solution.

17. The method of claim 3, wherein the starting composition and the recombinant microorganism or the enzyme preparation produced thereof are incubated under one or more of the following conditions:
pH of 7-8,
the amount of recombinant microorganism or the enzyme preparation constitutes 5%-30% by wet weight (w/v) of the mixture,
the at least one of rebaudioside A and stevioside is present at a concentration of 1-100 g/L;
trisodium citrate is present at 50-80 mM; and
sucrose is present at 30-90% (w/v).

18. The method of claim 17, wherein the amount of recombinant microorganism or the enzyme preparation constitutes 15% of the mixture, the at least one of rebaudioside A and stevioside is present at a concentration of 30 g/L; trisodium citrate is present at 60 mM, sucrose is present at 50% (w/v), and the pH is 7.3.

19. The method of claim 17, wherein the incubating step is performed at a temperature between 35-40° C. for a duration of 10-240 hours.

20. The method of claim 19, wherein the temperature is 39.5° C. and the duration is 120 hours.

21. The method of claim 19, wherein purifying rebaudioside D and/or rebaudioside M from the mixture comprises the following steps:
(a) heating, macro-filtering and ultra-filtering the mixture to obtain an ultrafiltrate;
(b) separating rebaudioside D and/or rebaudioside M from the ultrafiltrate by nanofiltration to obtain a retentate; and
(c) obtaining purified and concentrated rebaudioside D and/or rebaudioside M by concentrating the retentate to crystal and drying; or concentrating the retentate and spray-drying.

22. The method of claim 21, wherein the ultra-filtering in Step a uses an ultrafiltration membrane having a specification of 10 kD with a transmembrane pressure of 1.0-1.5 Megapascals (MPa).

23. The method of claim 21, wherein the nanofiltration in Step b uses a nanofiltration membrane having a specification of 0.5 kD with a transmembrane pressure of 1.5-2.0 MPa.

24. The method of claim 21, wherein the Step c comprises: concentrating the retentate to a liquid with a solid content of 10-30%, adding ethanol to adjust the ethanol concentration to 10-80%, heating to boil, cooling to 0-40° C. and crystallizing for 1-60 h.

25. The method of claim 21, wherein the spray-drying in Step c is performed under a condition in which the retentate is concentrated to a liquid with a solid content of 10-60% and then spray-dried with a temperature of 80° C. at an air inlet and 120° C. at an air outlet during spray-drying.

26. The method of claim 21, wherein the Steps a and b do not involve a multi-column system.

27. The method of claim 21, wherein the method does not involve a step of purifying the recombinant microorganism from a cell culture.

28. The method of claim 21, wherein the method does not involve a step of purifying the EUGT11 enzyme or the UGT76G1 enzyme.

* * * * *

SEQUENCE LISTING

```
<160> NUMBER OF SEQ ID NOS: 28

<210> SEQ ID NO 1
<211> LENGTH: 1510
<212> TYPE: DNA
<213> ORGANISM: Artificial Sequence
<220> FEATURE:
<223> OTHER INFORMATION: synthetic sequence

<400> SEQUENCE: 1
ggcccgctcg gccgctccac gcgcgcaccg gcccccttct tccgtcatgg actccggcta      60
ctcctcctcc tacgccgccg ccgccgggat gcacgtcgtg atctgcccgt ggctcgcctt     120
cggccacctg ctcccgtgcc tcgacctcgc ccagcgcctc gcgtcgcggg gccaccgcgt     180
gtcgttcgtc tccacgccgc ggaacatatc ccgcctcccg ccggtgcgcc ccgcgctcgc     240
gccgctcgtc gccttcgtgg cgctgccgct cccgcgcgtc gagggctcc ccgacggcgc      300 cgagtccacc aacgacgtcc cccacgacag gccggacatg gtcgagctcc accggagggc     360
cttcgacggg ctcgccgcgc ccttctcgga gttcttgggc accgcgtgcg ccgactgggt     420
```

-continued

```
catcgtcgac gtcttccacc actgggccgc agccgccgct ctcgagcaca aggtgccatg    480
tgcaatgatg ttgttgggct ctgcacatat gatcgcttcc atagcagaca dacggctcga    540
gcgcgcggag acagagtcgc ctgcggctgc cgggcaggga cgcccagcgg cggcgccaac    600
gttcgaggtg gcgaggatga agttgatacg aaccaaaggc tcatcgggaa tgtccctcgc    660
cgagcgcttc tccttgacgc tctcgaggag cagcctcgtc gtcgggcgga gctgcgtgga    720
gttcgagccg gagaccgtcc cgctcctgtc gacgctccgc ggtaagccta ttaccttcct    780
tggccttatg ccgccgttgc atgaaggccg ccgcgaggac ggcgaggatg ccaccgtccg    840
ctggctcgac gcgcagccgg ccaagtccgt cgtgtacgtc gcgctaggca gcgaggtgcc    900
actgggagtg gagaaggtcc acgagctcgc gctcgggctg gagctcgccg ggacgcgctt    960
cctctgggct cttaggaagc ccactggcgt ctccgacgcc gacctcctcc ccgccggctt   1020
cgaggagcgc acgcgcggcc gcggcgtcgt ggcgacgaga tgggttcctc agatgagcat   1080
actggcgcac gccgccgtgg gcgcgttcct gacccactgc ggctggaact cgaccatcga   1140
ggggctcatg ttcggccacc cgcttatcat gctgccgatc ttcggcgacc agggaccgaa   1200
cgcgcggcta atcgaggcga agaacgccgg attgcaggtg gcaagaaacg acggcgatgg   1260
atcgttcgac cgagaaggcg tcgcggcggc gattcgtgca gtcgcggtgg aggaagaaag   1320
cagcaaagtg tttcaagcca aagccaagaa gctgcaggag atcgtcgcgg acatggcctg   1380
ccatgagagg tacatcgacg gattcattca gcaattgaga tcttacaagg attgaagcat   1440
ctcaggatgt acacctgcaa cagtgcaact acaaaatcct tggaataaaa tgattttttgt   1500
tttgtagtcc                                                           1510
```

<210> SEQ ID NO 2
<211> LENGTH: 501
<212> TYPE: PRT
<213> ORGANISM: Artificial Sequence
<220> FEATURE:
<223> OTHER INFORMATION: synthetic sequence

<400> SEQUENCE: 2

```
Ala Arg Ser Ala Ala Pro Arg Ala His Arg Pro Pro Ser Ser Val Met
1               5                   10                  15

Asp Ser Gly Tyr Ser Ser Ser Tyr Ala Ala Ala Gly Met His Val
            20                  25                  30

Val Ile Cys Pro Trp Leu Ala Phe Gly His Leu Leu Pro Cys Leu Asp
        35                  40                  45

Leu Ala Gln Arg Leu Ala Ser Arg Gly His Arg Val Ser Phe Val Ser
    50                  55                  60

Thr Pro Arg Asn Ile Ser Arg Leu Pro Pro Val Arg Pro Ala Leu Ala
65                  70                  75                  80

Pro Leu Val Ala Phe Val Ala Leu Pro Leu Pro Arg Val Glu Gly Leu
                85                  90                  95

Pro Asp Gly Ala Glu Ser Thr Asn Asp Val Pro His Asp Arg Pro Asp
            100                 105                 110

Met Val Glu Leu His Arg Arg Ala Phe Asp Gly Leu Ala Ala Pro Phe
        115                 120                 125

Ser Glu Phe Leu Gly Thr Ala Cys Ala Asp Trp Val Ile Val Asp Val
    130                 135                 140

Phe His His Trp Ala Ala Ala Ala Leu Glu His Lys Val Pro Cys
145                 150                 155                 160

Ala Met Met Leu Leu Gly Ser Ala His Met Ile Ala Ser Ile Ala Asp
```

```
                    165                 170                 175

Arg Arg Leu Glu Arg Ala Glu Thr Glu Ser Pro Ala Ala Gly Gln
            180                 185                 190

Gly Arg Pro Ala Ala Pro Thr Phe Glu Val Ala Arg Met Lys Leu
        195                 200                 205

Ile Arg Thr Lys Gly Ser Ser Gly Met Ser Leu Ala Glu Arg Phe Ser
    210                 215                 220

Leu Thr Leu Ser Arg Ser Ser Leu Val Val Gly Arg Ser Cys Val Glu
225                 230                 235                 240

Phe Glu Pro Glu Thr Val Pro Leu Leu Ser Thr Leu Arg Gly Lys Pro
                245                 250                 255

Ile Thr Phe Leu Gly Leu Met Pro Pro Leu His Glu Gly Arg Arg Glu
            260                 265                 270

Asp Gly Glu Asp Ala Thr Val Arg Trp Leu Asp Ala Gln Pro Ala Lys
        275                 280                 285

Ser Val Val Tyr Val Ala Leu Gly Ser Glu Val Pro Leu Gly Val Glu
    290                 295                 300

Lys Val His Glu Leu Ala Leu Gly Leu Glu Leu Ala Gly Thr Arg Phe
305                 310                 315                 320

Leu Trp Ala Leu Arg Lys Pro Thr Gly Val Ser Asp Ala Asp Leu Leu
                325                 330                 335

Pro Ala Gly Phe Glu Glu Arg Thr Arg Gly Arg Gly Val Val Ala Thr
            340                 345                 350

Arg Trp Val Pro Gln Met Ser Ile Leu Ala His Ala Ala Val Gly Ala
        355                 360                 365

Phe Leu Thr His Cys Gly Trp Asn Ser Thr Ile Glu Gly Leu Met Phe
    370                 375                 380

Gly His Pro Leu Ile Met Leu Pro Ile Phe Gly Asp Gln Gly Pro Asn
385                 390                 395                 400

Ala Arg Leu Ile Glu Ala Lys Asn Ala Gly Leu Gln Val Ala Arg Asn
                405                 410                 415

Asp Gly Asp Gly Ser Phe Asp Arg Glu Gly Val Ala Ala Ile Arg
            420                 425                 430

Ala Val Ala Val Glu Glu Glu Ser Ser Lys Val Phe Gln Ala Lys Ala
        435                 440                 445

Lys Lys Leu Gln Glu Ile Val Ala Asp Met Ala Cys His Glu Arg Tyr
    450                 455                 460

Ile Asp Gly Phe Ile Gln Gln Leu Arg Ser Tyr Lys Asp Ser Ile Ser
465                 470                 475                 480

Gly Cys Thr Pro Ala Thr Val Gln Leu Gln Asn Pro Trp Asn Lys Met
                485                 490                 495

Ile Phe Val Leu Ser
            500

<210> SEQ ID NO 3
<211> LENGTH: 477
<212> TYPE: PRT
<213> ORGANISM: Artificial Sequence
<220> FEATURE:
<223> OTHER INFORMATION: synthetic sequence

<400> SEQUENCE: 3

Ala Arg Ser Ala Ala Pro Arg Ala His Arg Pro Pro Ser Ser Val Met
1               5                   10                  15

Asp Ser Gly Tyr Ser Ser Ser Tyr Ala Ala Ala Ala Gly Met His Val
```

```
                 20                  25                  30
Val Ile Cys Pro Trp Leu Ala Phe Gly His Leu Leu Pro Cys Leu Asp
             35                  40                  45

Leu Ala Gln Arg Leu Ala Ser Arg Gly His Arg Val Ser Phe Val Ser
         50                  55                  60

Thr Pro Arg Asn Ile Ser Arg Leu Pro Pro Val Arg Pro Ala Leu Ala
65                  70                  75                  80

Pro Leu Val Ala Phe Val Ala Leu Pro Leu Pro Arg Val Glu Gly Leu
                 85                  90                  95

Pro Asp Gly Ala Glu Ser Thr Asn Asp Val Pro His Asp Arg Pro Asp
             100                 105                 110

Met Val Glu Leu His Arg Arg Ala Phe Asp Gly Leu Ala Ala Pro Phe
         115                 120                 125

Ser Glu Phe Leu Gly Thr Ala Cys Ala Asp Trp Val Ile Val Asp Val
     130                 135                 140

Phe His His Trp Ala Ala Ala Ala Leu Glu His Lys Val Pro Cys
145                 150                 155                 160

Ala Met Met Leu Leu Gly Ser Ala His Met Ile Ala Ser Ile Ala Asp
                 165                 170                 175

Arg Arg Leu Glu Arg Ala Glu Thr Glu Ser Pro Ala Ala Gly Gln
             180                 185                 190

Gly Arg Pro Ala Ala Ala Pro Thr Phe Glu Val Ala Arg Met Lys Leu
         195                 200                 205

Ile Arg Thr Lys Gly Ser Ser Gly Met Ser Leu Ala Glu Arg Phe Ser
     210                 215                 220

Leu Thr Leu Ser Arg Ser Ser Leu Val Val Gly Arg Ser Cys Val Glu
225                 230                 235                 240

Phe Glu Pro Glu Thr Val Pro Leu Leu Ser Thr Leu Arg Gly Lys Pro
                 245                 250                 255

Ile Thr Phe Leu Gly Leu Met Pro Pro Leu His Glu Gly Arg Arg Glu
             260                 265                 270

Asp Gly Glu Asp Ala Thr Val Arg Trp Leu Asp Ala Gln Pro Ala Lys
         275                 280                 285

Ser Val Val Tyr Val Ala Leu Gly Ser Glu Val Pro Leu Gly Val Glu
     290                 295                 300

Lys Val His Glu Leu Ala Leu Gly Leu Glu Leu Ala Gly Thr Arg Phe
305                 310                 315                 320

Leu Trp Ala Leu Arg Lys Pro Thr Gly Val Ser Asp Ala Asp Leu Leu
                 325                 330                 335

Pro Ala Gly Phe Glu Glu Arg Thr Arg Gly Arg Gly Val Val Ala Thr
             340                 345                 350

Arg Trp Val Pro Gln Met Ser Ile Leu Ala His Ala Ala Val Gly Ala
         355                 360                 365

Phe Leu Thr His Cys Gly Trp Asn Ser Thr Ile Glu Gly Leu Met Phe
     370                 375                 380

Gly His Pro Leu Ile Met Leu Pro Ile Phe Gly Asp Gln Gly Pro Asn
385                 390                 395                 400

Ala Arg Leu Ile Glu Ala Lys Asn Ala Gly Leu Gln Val Ala Arg Asn
                 405                 410                 415

Asp Gly Asp Gly Ser Phe Asp Arg Glu Gly Val Ala Ala Ala Ile Arg
             420                 425                 430

Ala Val Ala Val Glu Glu Glu Ser Ser Lys Val Phe Gln Ala Lys Ala
         435                 440                 445
```

Lys Lys Leu Gln Glu Ile Val Ala Asp Met Ala Cys His Glu Arg Tyr
450                 455                 460

Ile Asp Gly Phe Ile Gln Gln Leu Arg Ser Tyr Lys Asp
465                 470                 475

<210> SEQ ID NO 4
<211> LENGTH: 1616
<212> TYPE: DNA
<213> ORGANISM: Artificial Sequence
<220> FEATURE:
<223> OTHER INFORMATION: synthetic sequence

<400> SEQUENCE: 4

```
cttgcgtgta aacgtcagtc aaacccaatg gaaaataaaa cggagaccac cgttcgccgg      60
cgccggagaa taatattatt cccggtacca tttcaaggcc acattaaccc aattcttcag     120
ctagccaatg tgttgtactc taaaggattc agtatcacca tctttcacac caacttcaac     180
aaacccaaaa catctaatta ccctcacttc actttcagat tcatcctcga caacgaccca     240
caagacgaac gcatttccaa tctaccgact catggtccgc tcgctggtat gcggattccg     300
attatcaacg aacacggagc tgacgaatta cgacgcgaac tggaactgtt gatgttagct     360
tctgaagaag atgaagaggt atcgtgttta atcacggatg ctctttggta cttcgcgcaa     420
tctgttgctg acagtcttaa cctccgacgg cttgttttga tgacaagcag cttgtttaat     480
tttcatgcac atgtttcact tcctcagttt gatgagcttg gttacctcga tcctgatgac     540
aaaacccgtt tggaagaaca agcgagtggg tttcctatgc taaaagtgaa agacatcaag     600
tctgcgtatt cgaactggca aatactcaaa gagatattag ggaagatgat aaaacaaaca     660
aaagcatctt caggagtcat ctggaactca tttaaggaac tcgaagagtc tgagctcgaa     720
actgttatcc gtgagatccc ggctccaagt ttcttgatac cactccccaa gcatttgaca     780
gcctcttcca gcagcttact agaccacgat cgaaccgttt ttcaatggtt agaccaacaa     840
ccgccaagtt cggtactgta tgttagtttt ggtagtacta gtgaagtgga tgagaaagat     900
ttcttggaaa tagctcgtgg gttggttgat agcaagcagt cgttttatg ggtggttcga      960
cctgggtttg tcaagggttc gacgtgggtc gaaccgttgc cagatgggtt cttgggtgaa    1020
agaggacgta ttgtgaaatg ggttccacag caagaagtgc tagctcatgg agcaataggc    1080
gcattctgga ctcatagcgg atggaactct acgttgaaaa gcgtttgtga aggtgttcct    1140
atgattttct cggatttggg gctcgatcaa ccgttgaatg ctagatacat gagtgatgtt    1200
ttgaaggtag gggtgtattt ggaaaatggg tgggaaagag agagatagc aaatgcaata    1260
agaagagtta tggtggatga agaaggagaa tacattagac agaatgcaag agttttgaaa    1320
caaaaggcag atgtttcttt gatgaagggt ggttcgtctt acgaatcatt agagtctcta    1380
gtttcttaca tttcatcgtt gtaaataaca cgatgattaa tcaagcactt ggattgcatg    1440
ctagctgagt agctgtaat tgagttatt agaagcaaag actacttggt ttaaattaaa    1500
taaaggatgg ttgttggtta tgtgagctag tttatgttat gttttgtagg ctataaaagc    1560
cttcatatgt ttcttattgt ttctgtttct aaggtgaaaa aatgctcgt ttttat        1616
```

<210> SEQ ID NO 5
<211> LENGTH: 531
<212> TYPE: PRT
<213> ORGANISM: Artificial Sequence
<220> FEATURE:
<223> OTHER INFORMATION: synthetic sequence

```
<400> SEQUENCE: 5

Leu Ala Cys Lys Arg Gln Ser Asn Pro Met Glu Asn Lys Thr Glu Thr
  1               5                  10                  15

Thr Val Arg Arg Arg Arg Ile Ile Leu Phe Pro Val Pro Phe Gln
             20                  25                  30

Gly His Ile Asn Pro Ile Leu Gln Leu Ala Asn Val Leu Tyr Ser Lys
                 35                  40                  45

Gly Phe Ser Ile Thr Ile Phe His Thr Asn Phe Asn Lys Pro Lys Thr
 50                  55                  60

Ser Asn Tyr Pro His Phe Thr Phe Arg Phe Ile Leu Asp Asn Asp Pro
 65                  70                  75                  80

Gln Asp Glu Arg Ile Ser Asn Leu Pro Thr His Gly Pro Leu Ala Gly
                 85                  90                  95

Met Arg Ile Pro Ile Ile Asn Glu His Gly Ala Asp Glu Leu Arg Arg
                100                 105                 110

Glu Leu Glu Leu Leu Met Leu Ala Ser Glu Glu Asp Glu Glu Val Ser
            115                 120                 125

Cys Leu Ile Thr Asp Ala Leu Trp Tyr Phe Ala Gln Ser Val Ala Asp
130                 135                 140

Ser Leu Asn Leu Arg Arg Leu Val Leu Met Thr Ser Ser Leu Phe Asn
145                 150                 155                 160

Phe His Ala His Val Ser Leu Pro Gln Phe Asp Glu Leu Gly Tyr Leu
                165                 170                 175

Asp Pro Asp Asp Lys Thr Arg Leu Glu Glu Gln Ala Ser Gly Phe Pro
            180                 185                 190

Met Leu Lys Val Lys Asp Ile Lys Ser Ala Tyr Ser Asn Trp Gln Ile
            195                 200                 205

Leu Lys Glu Ile Leu Gly Lys Met Ile Lys Gln Thr Lys Ala Ser Ser
210                 215                 220

Gly Val Ile Trp Asn Ser Phe Lys Glu Leu Glu Glu Ser Glu Leu Glu
225                 230                 235                 240

Thr Val Ile Arg Glu Ile Pro Ala Pro Ser Phe Leu Ile Pro Leu Pro
                245                 250                 255

Lys His Leu Thr Ala Ser Ser Ser Leu Leu Asp His Asp Arg Thr
            260                 265                 270

Val Phe Gln Trp Leu Asp Gln Gln Pro Pro Ser Ser Val Leu Tyr Val
            275                 280                 285

Ser Phe Gly Ser Thr Ser Glu Val Asp Glu Lys Asp Phe Leu Glu Ile
            290                 295                 300

Ala Arg Gly Leu Val Asp Ser Lys Gln Ser Phe Leu Trp Val Val Arg
305                 310                 315                 320

Pro Gly Phe Val Lys Gly Ser Thr Trp Val Glu Pro Leu Pro Asp Gly
                325                 330                 335

Phe Leu Gly Glu Arg Gly Arg Ile Val Lys Trp Val Pro Gln Gln Glu
            340                 345                 350

Val Leu Ala His Gly Ala Ile Gly Ala Phe Trp Thr His Ser Gly Trp
            355                 360                 365

Asn Ser Thr Leu Glu Ser Val Cys Glu Gly Val Pro Met Ile Phe Ser
370                 375                 380

Asp Phe Gly Leu Asp Gln Pro Leu Asn Ala Arg Tyr Met Ser Asp Val
385                 390                 395                 400

Leu Lys Val Gly Val Tyr Leu Glu Asn Gly Trp Glu Arg Gly Glu Ile
                405                 410                 415
```

```
Ala Asn Ala Ile Arg Arg Val Met Val Asp Glu Gly Glu Tyr Ile
            420                 425                 430

Arg Gln Asn Ala Arg Val Leu Lys Gln Lys Ala Asp Val Ser Leu Met
        435                 440                 445

Lys Gly Gly Ser Ser Tyr Glu Ser Leu Glu Ser Leu Val Ser Tyr Ile
    450                 455                 460

Ser Ser Leu Ile Thr Arg Leu Ile Lys His Leu Asp Cys Met Leu Ala
465                 470                 475                 480

Glu Leu Val Ile Val Ile Arg Ser Lys Asp Tyr Leu Val Ile Lys Arg
                485                 490                 495

Met Val Val Gly Tyr Val Ser Phe Met Leu Cys Phe Val Gly Tyr Lys
            500                 505                 510

Ser Leu His Met Phe Leu Ile Val Ser Val Ser Lys Val Lys Lys Met
        515                 520                 525

Leu Val Phe
    530

<210> SEQ ID NO 6
<211> LENGTH: 458
<212> TYPE: PRT
<213> ORGANISM: Artificial Sequence
<220> FEATURE:
<223> OTHER INFORMATION: synthetic sequence

<400> SEQUENCE: 6

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240
```

```
Ser Phe Leu Ile Pro Leu Pro Lys His Leu Thr Ala Ser Ser Ser Ser
            245                 250                 255

Leu Leu Asp His Asp Arg Thr Val Phe Gln Trp Leu Asp Gln Gln Pro
        260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 7
<211> LENGTH: 458
<212> TYPE: PRT
<213> ORGANISM: Artificial Sequence
<220> FEATURE:
<223> OTHER INFORMATION: synthetic sequence

<400> SEQUENCE: 7

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140
```

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
            165                 170                 175

Glu Gln Ala Ser Gly Phe Pro Met Leu Lys Val Lys Asp Ile Lys Ser
        180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
        210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 8
<211> LENGTH: 1266
<212> TYPE: DNA
<213> ORGANISM: Artificial Sequence
<220> FEATURE:
<223> OTHER INFORMATION: synthetic sequence

<400> SEQUENCE: 8
ggtttctcta tcaccatctt ccacaccaac ttcaacaaac cgaaaacctc taactacccg     60
cacttcacct tccgtttcat cctggacaac gacccgcagg acgaacgtat ctctaacctg    120
ccgacccacg gtccgctggc gggtatgcgt atcccgatca tcaacgaaca cggtgcggac    180
gaactgcgtc gtgaactgga actgctgatg ctggcgtctg aagaagacga agaagtttct    240

```
tgcctgatca ccgacgcgct gtggtacttc gcgcagtctg ttgcggactc tctgaacctg    300
cgtcgtctgg ttctgatgac ctcttctctg ttcaacttcc acgcgcacgt ttctctgccg    360
cagttcgacg aactgggtta cctggacccg gacgacaaaa cccgtctgga agaacaggcg    420
tctggtttcc cgatgctgaa agttaaagac atcaaatctg cgtactctaa ctggcagatc    480
ctgaaagaaa tcctgggtaa aatgatcaaa cagaccaaag cgtcttctgg tgttatctgg    540 aactcttca aagaactgga gaatctgaa ctggaaaccg ttatccgtga atcccggcg      600 ccgtctttcc tgatcccgct gccgaaacac ctgaccgcgt cttcttcttc tctgctggac    660
cacgaccgta ccgttttcca gtggctggac cagcagccgc cgtcttctgt tctgtacgtt    720
tctttcggtt ctacctctga gttgacgaa aaagacttcc tggaaatcgc gcgtggtctg    780
gttgactcta acagtctttt cctgtgggtt gttcgtccgg gtttcgttaa aggttctacc    840
tgggttgaac cgctgccgga cggtttcctg ggtgaacgtg gtcgtatcgt taaatgggtt    900
ccgcagcagg aagttctggc gcacggtgcg atcggtgcgt tctggaccca ctctggttgg    960
aactctaccc tggaatctgt tgcgaaggt gttccgatga tcttctctga cttcggtctg   1020
gaccagccgc tgaacgcgcg ttacatgtct gacgttctga agttggtgt ttacctggaa   1080 aacggttggg aacgtggtga atcgcgaac gcgatccgtc gtgttatggt tgacgaagaa   1140
ggtgaataca tccgtcagaa cgcgcgtgtt ctgaaacaga agcggacgt ttctctgatg   1200 aaaggtggtt cttcttacga atctctggaa tctctggttt cttacatctc ttctctgact   1260
agttaa                                                             1266
```

<210> SEQ ID NO 9
<211> LENGTH: 421
<212> TYPE: PRT
<213> ORGANISM: Artificial Sequence
<220> FEATURE:
<223> OTHER INFORMATION: synthetic sequence

<400> SEQUENCE: 9

```
Gly Phe Ser Ile Thr Ile Phe His Thr Asn Phe Asn Lys Pro Lys Thr
1               5                   10                  15

Ser Asn Tyr Pro His Phe Thr Phe Arg Phe Ile Leu Asp Asn Asp Pro
            20                  25                  30

Gln Asp Glu Arg Ile Ser Asn Leu Pro Thr His Gly Pro Leu Ala Gly
        35                  40                  45

Met Arg Ile Pro Ile Ile Asn Glu His Gly Ala Asp Glu Leu Arg Arg
    50                  55                  60

Glu Leu Glu Leu Leu Met Leu Ala Ser Glu Glu Asp Glu Glu Val Ser
65                  70                  75                  80

Cys Leu Ile Thr Asp Ala Leu Trp Tyr Phe Ala Gln Ser Val Ala Asp
                85                  90                  95

Ser Leu Asn Leu Arg Arg Leu Val Leu Met Thr Ser Ser Leu Phe Asn
            100                 105                 110

Phe His Ala His Val Ser Leu Pro Gln Phe Asp Glu Leu Gly Tyr Leu
        115                 120                 125

Asp Pro Asp Asp Lys Thr Arg Leu Glu Glu Gln Ala Ser Gly Phe Pro
    130                 135                 140

Met Leu Lys Val Lys Asp Ile Lys Ser Ala Tyr Ser Asn Trp Gln Ile
145                 150                 155                 160

Leu Lys Glu Ile Leu Gly Lys Met Ile Lys Gln Thr Lys Ala Ser Ser
                165                 170                 175
```

Gly Val Ile Trp Asn Ser Phe Lys Glu Leu Glu Ser Glu Leu Glu
            180                 185                 190

Thr Val Ile Arg Glu Ile Pro Ala Pro Ser Phe Leu Ile Pro Leu Pro
        195                 200                 205

Lys His Leu Thr Ala Ser Ser Ser Leu Leu Asp His Asp Arg Thr
    210                 215                 220

Val Phe Gln Trp Leu Asp Gln Gln Pro Pro Ser Ser Val Leu Tyr Val
225                 230                 235                 240

Ser Phe Gly Ser Thr Ser Glu Val Asp Glu Lys Asp Phe Leu Glu Ile
                245                 250                 255

Ala Arg Gly Leu Val Asp Ser Lys Gln Ser Phe Leu Trp Val Val Arg
            260                 265                 270

Pro Gly Phe Val Lys Gly Ser Thr Trp Val Glu Pro Leu Pro Asp Gly
        275                 280                 285

Phe Leu Gly Glu Arg Gly Arg Ile Val Lys Trp Val Pro Gln Gln Glu
    290                 295                 300

Val Leu Ala His Gly Ala Ile Gly Ala Phe Trp Thr His Ser Gly Trp
305                 310                 315                 320

Asn Ser Thr Leu Glu Ser Val Cys Glu Gly Val Pro Met Ile Phe Ser
                325                 330                 335

Asp Phe Gly Leu Asp Gln Pro Leu Asn Ala Arg Tyr Met Ser Asp Val
            340                 345                 350

Leu Lys Val Gly Val Tyr Leu Glu Asn Gly Trp Glu Arg Gly Glu Ile
        355                 360                 365

Ala Asn Ala Ile Arg Arg Val Met Val Asp Glu Glu Gly Glu Tyr Ile
    370                 375                 380

Arg Gln Asn Ala Arg Val Leu Lys Gln Lys Ala Asp Val Ser Leu Met
385                 390                 395                 400

Lys Gly Gly Ser Ser Tyr Glu Ser Leu Glu Ser Leu Val Ser Tyr Ile
                405                 410                 415

Ser Ser Leu Thr Ser
            420

<210> SEQ ID NO 10
<211> LENGTH: 373
<212> TYPE: PRT
<213> ORGANISM: Artificial Sequence
<220> FEATURE:
<223> OTHER INFORMATION: synthetic sequence

<400> SEQUENCE: 10

Met Arg Ile Pro Ile Ile Asn Glu His Gly Ala Asp Glu Leu Arg Arg
1               5                   10                  15

Glu Leu Glu Leu Leu Met Leu Ala Ser Glu Glu Asp Glu Glu Val Ser
                20                  25                  30

Cys Leu Ile Thr Asp Ala Leu Trp Tyr Phe Ala Gln Ser Val Ala Asp
            35                  40                  45

Ser Leu Asn Leu Arg Arg Leu Val Leu Met Thr Ser Ser Leu Phe Asn
        50                  55                  60

Phe His Ala His Val Ser Leu Pro Gln Phe Asp Glu Leu Gly Tyr Leu
65                  70                  75                  80

Asp Pro Asp Asp Lys Thr Arg Leu Glu Glu Gln Ala Ser Gly Phe Pro
                85                  90                  95

Met Leu Lys Val Lys Asp Ile Lys Ser Ala Tyr Ser Asn Trp Gln Ile
            100                 105                 110

Leu Lys Glu Ile Leu Gly Lys Met Ile Lys Gln Thr Lys Ala Ser Ser
            115                 120                 125

Gly Val Ile Trp Asn Ser Phe Lys Glu Leu Glu Ser Glu Leu Glu
        130                 135                 140

Thr Val Ile Arg Glu Ile Pro Ala Pro Ser Phe Leu Ile Pro Leu Pro
145                 150                 155                 160

Lys His Leu Thr Ala Ser Ser Ser Leu Leu Asp His Asp Arg Thr
            165                 170                 175

Val Phe Gln Trp Leu Asp Gln Gln Pro Ser Ser Val Leu Tyr Val
            180                 185                 190

Ser Phe Gly Ser Thr Ser Glu Val Asp Glu Lys Asp Phe Leu Glu Ile
            195                 200                 205

Ala Arg Gly Leu Val Asp Ser Lys Gln Ser Phe Leu Trp Val Val Arg
    210                 215                 220

Pro Gly Phe Val Lys Gly Ser Thr Trp Val Glu Pro Leu Pro Asp Gly
225                 230                 235                 240

Phe Leu Gly Glu Arg Gly Arg Ile Val Lys Trp Val Pro Gln Gln Glu
                245                 250                 255

Val Leu Ala His Gly Ala Ile Gly Ala Phe Trp Thr His Ser Gly Trp
            260                 265                 270

Asn Ser Thr Leu Glu Ser Val Cys Glu Gly Val Pro Met Ile Phe Ser
            275                 280                 285

Asp Phe Gly Leu Asp Gln Pro Leu Asn Ala Arg Tyr Met Ser Asp Val
            290                 295                 300

Leu Lys Val Gly Val Tyr Leu Glu Asn Gly Trp Glu Arg Gly Glu Ile
305                 310                 315                 320

Ala Asn Ala Ile Arg Arg Val Met Val Asp Glu Gly Glu Tyr Ile
                325                 330                 335

Arg Gln Asn Ala Arg Val Leu Lys Gln Lys Ala Asp Val Ser Leu Met
            340                 345                 350

Lys Gly Gly Ser Ser Tyr Glu Ser Leu Glu Ser Leu Val Ser Tyr Ile
            355                 360                 365

Ser Ser Leu Thr Ser
    370

<210> SEQ ID NO 11
<211> LENGTH: 60
<212> TYPE: DNA
<213> ORGANISM: Artificial Sequence
<220> FEATURE:
<223> OTHER INFORMATION: synthetic sequence

<400> SEQUENCE: 11
gcagccgttc gtggaagggc caatgacttg ggtcgtaagc acctgcattt atttccgttc    60

<210> SEQ ID NO 12
<211> LENGTH: 60
<212> TYPE: DNA
<213> ORGANISM: Artificial Sequence
<220> FEATURE:
<223> OTHER INFORMATION: synthetic sequence

<400> SEQUENCE: 12
cgatcgtaca tatccagctc ttgttaccgg aagtatgggt tgtagatatg gtcgcccgcc    60

<210> SEQ ID NO 13
<211> LENGTH: 60
<212> TYPE: DNA

<213> ORGANISM: Artificial Sequence
<220> FEATURE:
<223> OTHER INFORMATION: synthetic sequence

<400> SEQUENCE: 13

```
agaaaccgtt ggcatctatc gcatatacgg tgtccggcgg ttgttgatac ttcgcgctaa    60
```

<210> SEQ ID NO 14
<211> LENGTH: 60
<212> TYPE: DNA
<213> ORGANISM: Artificial Sequence
<220> FEATURE:
<223> OTHER INFORMATION: synthetic sequence

<400> SEQUENCE: 14

```
ctcgcttttc ccgtcttccc ttgtacagac caatatgggg accaattttt gctgtgtcat    60
```

<210> SEQ ID NO 15
<211> LENGTH: 1515
<212> TYPE: DNA
<213> ORGANISM: Artificial Sequence
<220> FEATURE:
<223> OTHER INFORMATION: synthetic sequence

<400> SEQUENCE: 15

```
atgaaaaaca aggtgcagct catcacttac gccgaccgcc ttggcgacgg caccatcaag      60
tcgatgaccg acattctgcg cacccgcttc gacggcgtgt acgacggcgt tcacatcctg     120
ccgttcttca ccccgttcga cggcgccgac gcaggcttcg acccgatcga ccacaccaag     180
gtcgacgaac gtctcggcag ctgggacgac gtcgccgaac tctccaagac ccacaacatc     240
atggtcgacg ccatcgtcaa ccacatgagt tgggaatcca gcagttccag gacgtgctg     300
gccaagggcg aggagtccga atactatccg atgttcctca ccatgagctc cgtgttcccg     360
aacggcgcca ccgaagagga cctggccggc atctaccgtc gcgtccgggg cctgccgttc     420
acccactaca agttcgccgg caagaccccgc ctcgtgtggg tcagcttcac cccgcagcag    480
gtggacatcg acaccgattc cgacaagggt tgggaatacc tcatgtcgat tttcgaccag    540
atggccgcct ctcacgtcag ctacatccgc ctcgacgccg tcggctatgg cgccaaggaa    600
gccggcacca gctgcttcat gaccccgaag accttcaagc tgatctcccg tctgcgtgag    660
gaaggcgtca gcgcggtct ggaaatcctc atcgaagtgc actcctacta caagaagcag    720
gtcgaaatcg catccaaggt ggaccgcgtc tacgacttcg ccctgcctcc gctgctgctg    780
cacgcgctga gcaccggcca cgtcgagccc gtcgcccact ggaccgacat cgcccgaac    840
aacgccgtca ccgtgctcga tacgcacgac ggcatcggcg tgatcgacat cggctccgac    900
cagctcgacc gctcgctcaa gggtctcgtg ccggatgagg acgtggacaa cctcgtcaac    960
accatccacg ccaacaccca cggcgaatcc caggcagcca ctggcgccgc cgcatccaat   1020
ctcgacctct accaggtcaa cagcacctac tattcggcgc tcgggtgcaa cgaccagcac   1080
tacatcgccg cccgcgcggt gcagttcttc ctgccgggcg tgccgcaagt ctactacgtc   1140
ggcgcgctcg ccggcaagaa cgacatggag ctgctgcgta agacgaataa cggccgcgac   1200
atcaatcgcc attactactc caccgcggaa atcgacgaga acctcaagcg tccggtcgtc   1260
aaggccctga acgcgctcgc caagttccgc aacgagctcg acgcgttcga cggcacgttc   1320
tcgtacacca ccgatgacga cacgtccatc agcttcacct ggcgcggcga aaccagccag   1380
gccacgctga cgttcgagcc gaagcgcggt ctcggtgtgg acaacactac gccggtcgcc   1440
atgttggaat gggaggattc cgcgggagac caccgttcgg atgatctgat cgccaatccg   1500
```
cctgtcgtcg cctga                                                                           1515

<210> SEQ ID NO 16
<211> LENGTH: 504
<212> TYPE: PRT
<213> ORGANISM: Artificial Sequence
<220> FEATURE:
<223> OTHER INFORMATION: synthetic sequence

<400> SEQUENCE: 16

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
        275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
            340                 345                 350
```

```
Ala Leu Gly Cys Asn Asp Gln His Tyr Ile Ala Ala Arg Ala Val Gln
            355                 360                 365

Phe Phe Leu Pro Gly Val Pro Gln Val Tyr Tyr Val Gly Ala Leu Ala
        370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Asp Thr
        435                 440                 445

Ser Ile Ser Phe Thr Trp Arg Gly Glu Thr Ser Gln Ala Thr Leu Thr
    450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
                485                 490                 495

Ile Ala Asn Pro Pro Val Val Ala
            500

<210> SEQ ID NO 17
<211> LENGTH: 1467
<212> TYPE: DNA
<213> ORGANISM: Artificial Sequence
<220> FEATURE:
<223> OTHER INFORMATION: synthetic sequence

<400> SEQUENCE: 17
atgtttgccg aagatctgaa acggacggag aagatgacag tggacgacgt gttcgagcag      60
tcggcgcaga gatgcgcga gcagggcatg agcgagatcg ccatctcgca gttcaggcac     120
gcataccatg tgtgggccag cgagaaggag agcgcgtgga tccgcgagga cgccgtcgag     180
ccgctgcacg gcgtgcggag cttccatgac gtgtacaaga ccatcgatca tgacaaggca     240
gtgcacgcgt tcgccaagac tgcattcctc aagctcaacg gcggcctggg aacctcgatg     300
ggcctgcaat gcgcgaagtc gctgctgccg gtgcgccgcc acaaggctcg gcagatgcgc     360
ttcctcgaca tcatcctcgg tcaggtgctc accgcgcgca cgaggctgaa cgtgcctctg     420
ccggtcacgt tcatgaactc gttccgcact tcggatgaca cgatgaaggc actgcgacac     480
cagcgcaagt tcaagcagac cgacatcccg ctggagatca tccagcatca ggaaccgaag     540
atcgacgcgg ccaccggggc gccggcgtct tggccggcca ccccgatct ggagtggtgc     600 ccgcccggcc acggcgacct gttctcgacg ctgtgggagt ccggcctgct ggacactctg     660
ctggagcatg gcttcgaata cctgttcatc tcgaactccg acaatttggg tgcgcgcccg     720
tctcgcacgc tcgcccagta tttcgaggat acgggcgccc cgttcatggt cgaggtcgcc     780
aatcgcacgt acgcggaccg caagggtggc catatcgtgc gcgacaccgg caccggccga     840
ctgatcctgc gggagatgtc gcaggtgcat cctgacgaca aggacgcggc ccaggacatc     900
gccaagcacc gtatttcaa cacgaacaac atctgggtgc gatcgacgt gctgcgcgtc     960 atgctcgccg agcatgacgg cgtgctgccg cttccgtca tcatcaacaa caagaccgtc    1020
gacccgaccg accccagtc cccggcggtg gtccagctgg agactgcgat gggcgcggcg    1080
atcggcctgt cgaaggcgc gatctgtgtg caggtggacc gcatgcggtt cctgccagtg    1140
aagacgacca cgacctgtt cattatgcgt tccgatcggt tccaccttac ggactcgtat    1200
```

```
gagatggagg acggcaacta cattttcccg aacgtcgacc tcgatccgcg gtactacaag    1260
aacatcgagg acttcaacga acggttcccc tacaacgtgc cgtcgctcgc cgccgcgaac    1320
tcggtcagca tcaagggaga ctggacattc ggacgtgacg tcatcatgtt cgccgacgcg    1380
cgtctggagg atagaaacga gcccagttac gtacccaacg gcgaatacgt cggaccgatg    1440
ggcatcgagc ccggtgattg ggtgtga                                         1467
```

<210> SEQ ID NO 18
<211> LENGTH: 488
<212> TYPE: PRT
<213> ORGANISM: Artificial Sequence
<220> FEATURE:
<223> OTHER INFORMATION: synthetic sequence

<400> SEQUENCE: 18

```
Met Phe Ala Glu Asp Leu Lys Arg Thr Glu Lys Met Thr Val Asp Asp
 1               5                  10                  15

Val Phe Glu Gln Ser Ala Gln Lys Met Arg Glu Gln Gly Met Ser Glu
            20                  25                  30

Ile Ala Ile Ser Gln Phe Arg His Ala Tyr His Val Trp Ala Ser Glu
        35                  40                  45

Lys Glu Ser Ala Trp Ile Arg Glu Asp Ala Val Glu Pro Leu His Gly
    50                  55                  60

Val Arg Ser Phe His Asp Val Tyr Lys Thr Ile Asp His Asp Lys Ala
65                  70                  75                  80

Val His Ala Phe Ala Lys Thr Ala Phe Leu Lys Leu Asn Gly Gly Leu
                85                  90                  95

Gly Thr Ser Met Gly Leu Gln Cys Ala Lys Ser Leu Leu Pro Val Arg
            100                 105                 110

Arg His Lys Ala Arg Gln Met Arg Phe Leu Asp Ile Ile Leu Gly Gln
        115                 120                 125

Val Leu Thr Ala Arg Thr Arg Leu Asn Val Pro Leu Pro Val Thr Phe
    130                 135                 140

Met Asn Ser Phe Arg Thr Ser Asp Asp Thr Met Lys Ala Leu Arg His
145                 150                 155                 160

Gln Arg Lys Phe Lys Gln Thr Asp Ile Pro Leu Glu Ile Ile Gln His
                165                 170                 175

Gln Glu Pro Lys Ile Asp Ala Ala Thr Gly Ala Pro Ala Ser Trp Pro
            180                 185                 190

Ala Asn Pro Asp Leu Glu Trp Cys Pro Pro Gly His Gly Asp Leu Phe
        195                 200                 205

Ser Thr Leu Trp Glu Ser Gly Leu Leu Asp Thr Leu Leu Glu His Gly
    210                 215                 220

Phe Glu Tyr Leu Phe Ile Ser Asn Ser Asp Asn Leu Gly Ala Arg Pro
225                 230                 235                 240

Ser Arg Thr Leu Ala Gln Tyr Phe Glu Asp Thr Gly Ala Pro Phe Met
                245                 250                 255

Val Glu Val Ala Asn Arg Thr Tyr Ala Asp Arg Lys Gly Gly His Ile
            260                 265                 270

Val Arg Asp Thr Ala Thr Gly Arg Leu Ile Leu Arg Glu Met Ser Gln
        275                 280                 285

Val His Pro Asp Asp Lys Asp Ala Ala Gln Asp Ile Ala Lys His Pro
    290                 295                 300

Tyr Phe Asn Thr Asn Asn Ile Trp Val Arg Ile Asp Val Leu Arg Val
```

```
                305                 310                 315                 320
Met Leu Ala Glu His Asp Gly Val Leu Pro Leu Pro Val Ile Ile Asn
                    325                 330                 335

Asn Lys Thr Val Asp Pro Thr Asp Pro Gln Ser Pro Ala Val Val Gln
                340                 345                 350

Leu Glu Thr Ala Met Gly Ala Ala Ile Gly Leu Phe Glu Gly Ala Ile
            355                 360                 365

Cys Val Gln Val Asp Arg Met Arg Phe Leu Pro Val Lys Thr Thr Asn
        370                 375                 380

Asp Leu Phe Ile Met Arg Ser Asp Arg Phe His Leu Thr Asp Ser Tyr
385                 390                 395                 400

Glu Met Glu Asp Gly Asn Tyr Ile Phe Pro Asn Val Asp Leu Asp Pro
                405                 410                 415

Arg Tyr Tyr Lys Asn Ile Glu Asp Phe Asn Arg Phe Pro Tyr Asn
                    420                 425                 430

Val Pro Ser Leu Ala Ala Ala Asn Ser Val Ser Ile Lys Gly Asp Trp
                435                 440                 445

Thr Phe Gly Arg Asp Val Ile Met Phe Ala Asp Ala Arg Leu Glu Asp
            450                 455                 460

Arg Asn Glu Pro Ser Tyr Val Pro Asn Gly Glu Tyr Val Gly Pro Met
465                 470                 475                 480

Gly Ile Glu Pro Gly Asp Trp Val
                    485

<210> SEQ ID NO 19
<211> LENGTH: 30
<212> TYPE: DNA
<213> ORGANISM: Artificial Sequence
<220> FEATURE:
<223> OTHER INFORMATION: synthetic sequence

<400> SEQUENCE: 19
cgcggatcca tggactccgg ctactcctcc                                    30

<210> SEQ ID NO 20
<211> LENGTH: 34
<212> TYPE: DNA
<213> ORGANISM: Artificial Sequence
<220> FEATURE:
<223> OTHER INFORMATION: synthetic sequence

<400> SEQUENCE: 20
cccaagcttt caatccttgt aagatctcaa ttgc                               34

<210> SEQ ID NO 21
<211> LENGTH: 33
<212> TYPE: DNA
<213> ORGANISM: Artificial Sequence
<220> FEATURE:
<223> OTHER INFORMATION: synthetic sequence

<400> SEQUENCE: 21
catgccatgg aaaacaaaac cgaaaccacc gtt                                33

<210> SEQ ID NO 22
<211> LENGTH: 32
<212> TYPE: DNA
<213> ORGANISM: Artificial Sequence
<220> FEATURE:
<223> OTHER INFORMATION: synthetic sequence
```

```
<400> SEQUENCE: 22
ggactagttt aactagtcag agaagagatg ta                             32

<210> SEQ ID NO 23
<211> LENGTH: 32
<212> TYPE: DNA
<213> ORGANISM: Artificial Sequence
<220> FEATURE:
<223> OTHER INFORMATION: synthetic sequence

<400> SEQUENCE: 23
ccggaattca aacaaaacc gaaaccaccg tt                              32

<210> SEQ ID NO 24
<211> LENGTH: 36
<212> TYPE: DNA
<213> ORGANISM: Artificial Sequence
<220> FEATURE:
<223> OTHER INFORMATION: synthetic sequence

<400> SEQUENCE: 24
cggggtacct cattaactag tcagagaaga gatgta                         36

<210> SEQ ID NO 25
<211> LENGTH: 32
<212> TYPE: DNA
<213> ORGANISM: Artificial Sequence
<220> FEATURE:
<223> OTHER INFORMATION: synthetic sequence

<400> SEQUENCE: 25
ccggaattca aacaaaacc gaaaccaccg tt                              32

<210> SEQ ID NO 26
<211> LENGTH: 32
<212> TYPE: DNA
<213> ORGANISM: Artificial Sequence
<220> FEATURE:
<223> OTHER INFORMATION: synthetic sequence

<400> SEQUENCE: 26
ggactagttt aactagtcag agaagagatg ta                             32

<210> SEQ ID NO 27
<211> LENGTH: 41
<212> TYPE: DNA
<213> ORGANISM: Artificial Sequence
<220> FEATURE:
<223> OTHER INFORMATION: synthetic sequence

<400> SEQUENCE: 27
ccgctcgagt catcattatt agcttacttt cataattgcg a                   41

<210> SEQ ID NO 28
<211> LENGTH: 36
<212> TYPE: DNA
<213> ORGANISM: Artificial Sequence
<220> FEATURE:
<223> OTHER INFORMATION: synthetic sequence

<400> SEQUENCE: 28
atttgcggcc gcttaactag tcagagaaga gatgta                         36
```